United States Patent
Liu et al.

(10) Patent No.: US 11,697,639 B2
(45) Date of Patent: Jul. 11, 2023

(54) QUATERNARY AMMONIUM SALT COMPOUND, PREPARATION METHOD THEREFOR AND USE THEREOF

(71) Applicant: WEST CHINA HOSPITAL, SICHUAN UNIVERSITY, Sichuan (CN)

(72) Inventors: Jin Liu, Sichuan (CN); Bowen Ke, Sichuan (CN); Wensheng Zhang, Sichuan (CN); Jun Yang, Sichuan (CN); Lei Tang, Sichuan (CN)

(73) Assignee: WEST CHINA HOSPITAL, SICHUAN UNIVERSITY, Sichuan (CN)

( * ) Notice: Subject to any disclaimer, the term of this patent is extended or adjusted under 35 U.S.C. 154(b) by 0 days.

(21) Appl. No.: 16/969,005

(22) PCT Filed: Jan. 31, 2019

(86) PCT No.: PCT/CN2019/074275
§ 371 (c)(1),
(2) Date: Dec. 22, 2020

(87) PCT Pub. No.: WO2019/154287
PCT Pub. Date: Aug. 15, 2019

(65) Prior Publication Data
US 2021/0107872 A1 Apr. 15, 2021

(30) Foreign Application Priority Data
Feb. 11, 2018 (CN) .......................... 201810144661.X

(51) Int. Cl.
| | | |
|---|---|---|
| C07D 207/02 | (2006.01) | |
| C07D 211/60 | (2006.01) | |
| C07C 231/12 | (2006.01) | |
| C07C 237/04 | (2006.01) | |
| C07D 205/04 | (2006.01) | |
| C07D 207/16 | (2006.01) | |
| C07D 223/06 | (2006.01) | |
| C07D 225/02 | (2006.01) | |

(52) U.S. Cl.
CPC .......... *C07D 211/60* (2013.01); *C07C 231/12* (2013.01); *C07C 237/04* (2013.01); *C07D 205/04* (2013.01); *C07D 207/16* (2013.01); *C07D 223/06* (2013.01); *C07D 225/02* (2013.01)

(58) Field of Classification Search
CPC .................................................. C07D 207/02
See application file for complete search history.

(56) References Cited

FOREIGN PATENT DOCUMENTS

| CN | 1295558 A | * | 5/2001 | .............. A61P 23/02 |
|---|---|---|---|---|
| CN | 1295558 A | | 5/2001 | |
| CN | 103601650 A | | 2/2014 | |

OTHER PUBLICATIONS

Han, H. "Targeted Prodrug Design to Optimize Drug Delivery." AAPS Pharmsci. (2000), vol. 2 (1) article 6, pp. 1-11. (Year: 2000).*
Ettmayer, P., et al. "Lessons Learned from Marketed and Investigational Prodrugs." J. Med. Chem. (2004) 47(10), pp. 2393-2404. (Year: 2004).*
Testa, B. "Prodrug research: futile or fertile?" Biochem. Pharm. (2004) 68, pp. 2097-2106. (Year: 2004).*

* cited by examiner

*Primary Examiner* — John S Kenyon
(74) *Attorney, Agent, or Firm* — NKL Law; Allen Xue

(57) ABSTRACT

A compound is shown in formula I and can be in the form of a pharmaceutically acceptable salt, or a stereoisomer, or a solvate, or a prodrug, or a metabolite. The compound takes effect rapidly and has a long-time local anesthetic effect following a single dose, with the sensory nerve blocking time being greater than the motor nerve blocking time, has both a long-acting local anesthetic effect and a selective local anesthetic effect, significantly reduces side effects of the compositions QX314 and QX314 and a quaternary ammonium salt compound with surfactant structural characteristics, and is safer. The compound of formula I of the present invention and a pharmaceutically acceptable salt thereof can be used for preparing drugs that have a long-time local anesthetic effect and a selective local anesthetic effect.

20 Claims, No Drawings

QUATERNARY AMMONIUM SALT COMPOUND, PREPARATION METHOD THEREFOR AND USE THEREOF

TECHNICAL FIELD

The present invention relates to a quaternary ammonium compound, as well as the preparative method and the use thereof.

BACKGROUND ART

Local anesthetics is a class of drugs that can reversibly block the occurrence and transmission of sensory nerve impulses in the administration area. Under the condition that animals or humans are waking and conscious, it can locally and reversibly block the generation and signal conduction of sensory nerve impulse, resulting in the temporary sensory loss in the innervated area, and thereby reversibly causing the loss of local tissue pain. Generally, the effect of local anesthetics is limited to the administration site and disappears rapidly as the drug diffuses from the administration site. Local anesthetics block the generation of action potentials and the conduction of nerve impulses by directly inhibiting the related ion channels in nerve cells and fiber membranes, thereby producing local anesthesia. Currently, the well-known action mechanism for local anesthetics is blocking voltage-gated $Na^+$ channels in nerve cell membranes, inhibiting nerve impulses, and producing local anesthesia.

The local anesthetics currently used in clinical practice are all hydrophobic compounds without electric charge, so they can easily enter nerve cells through cell membranes by diffusion and permeation, to reach the blocking site of sodium channels. These anesthetics block sodium channels and thereby interrupt the excitability of neurons. In fact, although these local anesthetic molecules can easily enter nerve cells by diffusion to exert their actions, they also easily diffuse rapidly from the drug delivery site by diffusion, thereby liberating nerve cells and resulting in that the local anesthetic effect cannot be kept for a long time. Even if the dosage is increased, the local anesthesia time can only be prolonged to a certain extent. These local anesthetic drugs cannot realize the ideal effect of long-term local anesthesia. At present, most of the local anesthetics commonly used in clinical have an action time of less than 4 hours. Because traditional local anesthetics last for a short period of time, analgesic pumps have to be used to maintain nerve block. The use of catheters in the spinal canal, nerve roots, and subcutaneous locations has greatly increased medical costs and the incidence of infection.

On the other hand, traditional local anesthetics do not have specific selectivity for nerve blocking. They block a variety of nerve fibers extensively during use, and affect various nerve functions such as sensation, pain, movement, and sympathetic nerves. This pharmacological feature greatly limits the wide application of local anesthetics in clinical practice. For example, early functional exercise and rehabilitation of patients after knee replacement is particularly important, however, there are no drugs that selectively block pain in the current local anesthetics. Most of surgical patients who use local anesthetics experience the motor nerves being blocked, unable to restore motor function, that limits postoperative rehabilitation. The research on local anesthetics urgently needs to introduce new research ideas and develop long-acting local anesthetics that selectively block sensory function, without affecting motor function, to meet clinical requirements.

The chemical structure of traditional local anesthetics generally contains at least one non-amide tertiary N atom. When N is substituted, the corresponding quaternary ammonium compound will be obtained. The molecular structure of the quaternary ammonium compound has a positive charge, and the ability to penetrate the cell membrane is significantly reduced. For example, ethyl substitution of the tertiary amine N atom in lidocaine will produce a quaternary ammonium compound called QX-314 (Formula II). Similar to QX-314, QX-222 (Formula III) is also another quaternary ammonium salt having similar structure. Under special conditions, QX-314 and QX-222 may produce local anesthesia. Because the structures of QX-314 and QX-222 have positive charges, they cannot pass through cell membranes under normal conditions, and thus cannot quickly produce local anesthesia. But once it passes through the cell membrane, it can significantly inhibit sodium ion channels in nerve cells, resulting in a lasting local anesthetic effect (Courtney KR. *J Pharmacol Exp Ther.* 1975, 195:225-236). Current research has found that QX-314 can easily enter nerve cells through the activation of TRPV1 channel with the assistance of capsaicin (transient receptor potential channel vanilloid subtype 1 agonist, TRPV1 Agonist), producing a long-term nerve block (Craig R. Ries. *Anesthesiology* 2009; 111:122-126). However, the strong irritation of capsaicin makes it difficult to have application prospects.

Although studies have shown that the combination of QX314 and local anesthetics clinically used such as bupivacaine and lidocaine can quickly produce anesthesia and avoid the irritation of capsaicin. However, the synergistic use of above drugs still cannot achieve the expected effect of local anesthesia. With the addition of surfactants, it can also help QX314 enter the cell membrane and cause local anesthesia for more than 8 hours (Daniel S. Kohane, *PNAS.* 2010; 107: 3745-3750).

The current research has shown that the safety problems of QX314 are mainly manifested as local nerve damage, and the death of experimental animals during intrathecal injection and so on. On the basis of QX-314, a series of long-chain compounds with surfactant structure have been developed, and this kind of compound can realize a longer local anesthetic effect to a certain extent. Because this kind of compound has a surfactant-like structure, although it can produce long-acting effect at a certain degree, it will also cause serious muscle and nerve damage in local injection site, with poor safety. Meanwhile, similar compounds that have been reported so far do not have selective local anesthesia, and cannot meet clinical needs. Therefore, whether QX314 is used alone, or it is used in combination with other active drugs, or long-chain compounds of QX314 have structural characteristics of surfactant, with the disadvantages of poor safety and poor selectivity for local anesthesia.

Content of the Invention

In view of above-mentioned problems, the present invention provides a new class of quaternary ammonium compounds, which have both long-acting and selective local anesthesia (the block time of sensory nerve is longer than that of motor nerve), and the compound has the advantages of long-time local anesthetic action, good local anesthetic selectivity, less nerve damage, and high safety, compared with the existing QX314, QX314 composition, and the long-chain compound with surfactant structure characteristics.

The present invention provides compound of formula (I), or pharmaceutically acceptable salts thereof, or stereoisomers thereof, or solvates thereof, or prodrugs thereof, or metabolites thereof:

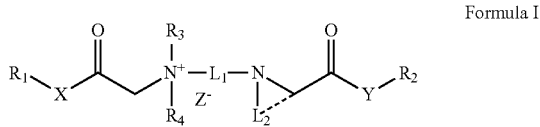

Formula I

Wherein,

X and Y are each independently selected from O, S, and $NR_{10}$, in which $R_{10}$ is selected from H, deuterium or $C_{1-4}$ alkyl;

$Z^-$ is pharmaceutically acceptable anions;

$R_1$ is selected from the aryls substituted by $n_1$ $R_{11}$ groups;

$R_2$ is selected from the aryls substituted by $n_1'R_{11}'$ groups;

Wherein, $n_1$ and $n_1'$ are independently of each other selected from an integer of 0-5, and $R_{11}$ and $R_{11}'$ are independently of each other selected from the group consisting of deuterium, $C_{1-4}$ alkyls, $C_{1-4}$ alkoxys, halogen, nitro, cyano, hydroxyl, carboxyl, amino, thiol, and ester group;

Provided that one of $R_3$ and $R_4$ is $C_1$ alkyl, the other can be independently selected from $C_{1-4}$ alkyls;

Provided that one of $R_3$ and $R_4$ is $C_2$ alkyl, the other can be independently selected from $C_1$, $C_3$, $C_4$ alkyls;

Provided that one of $R_3$ and $R_4$ is $C_3$ alkyl, the other can be independently selected from $C_{3-4}$ alkyls;

Provided that one of $R_3$ and $R_4$ is $C_4$ alkyl, the other can be independently selected from $C_4$ alkyl;

$L_1$ is selected from substituted or unsubstituted $C_{1-14}$ alkylenyl; wherein, the main chain of said alkylenyl contains 0-4 heteroatoms, and said heteroatoms are selected from O, S, and $NR_{12}$, in which said $R_{12}$ is selected from hydrogen, deuterium, $C_{1-4}$ alkyl, and $C_{1-4}$ alkoxy; said substituent is deuterium, $C_{1-4}$ alkyl, $C_{1-4}$ alkoxy, and halogen;

When the dashed line in formula I is none, $L_2$ is selected from hydrogen, deuterium, substituted or unsubstituted $C_{1-8}$ alkyl, and substituted or unsubstituted $C_{1-8}$ alkoxy, in which said substituent is deuterium, $C_{1-4}$ alkyl, $C_{1-4}$ alkoxy, and halogen;

When the dashed line in formula I is a bond, $L_2$ is selected from substituted or unsubstituted $C_{1-8}$ alkylenyl, in which the substituent is deuterium, $C_{1-4}$ alkyl, $C_{1-4}$ alkoxy, and halogen.

Further, said pharmaceutically acceptable anion $Z^-$ is a halogen anion, sulfate, acetate, tartrate, p-toluenesulfonate, methanesulfonate, and citrate.

Further, said pharmaceutically acceptable anion $Z^-$ is a halogen anion.

Further, said pharmaceutically acceptable anion $Z^-$ is Br.

Further, pharmaceutically acceptable salts of said compound denote those formed by compound of formula I and pharmaceutically acceptable inorganic acid or organic acid.

Further, said inorganic acid or organic acid is hydrochloric acid, hydrobromic acid, acetic acid, sulfuric acid, methanesulfonic acid, p-toluenesulfonic acid, carbonic acid, tartaric acid, lauric acid, maleic acid, citric acid or benzoic acid.

Further, X and Y are each independently selected from O, S, or $NR_{10}$, in which $R_{10}$ is selected from H, deuterium or $C_{1-2}$ alkyl;

Further, $R_1$ is selected from the aryls substituted by $n_1$ $R_{11}$ groups;

$R_2$ is selected from the aryls substituted by $n_1'R_{11}'$ groups;

Wherein, $n_1$ and $n_1'$ are independently of each other selected from an integer of 0-5, and $R_{11}$ and $R_{11}'$ are independently of each other selected from the group consisting of deuterium, $C_{1-4}$ alkyls, $C_{1-4}$ alkoxys, halogen, nitro, cyano, hydroxyl, carboxyl, amino, thiol, and ester group;

Provided that $R_3$ is $C_1$ alkyl, $R_4$ can be independently selected from $C_{1-2}$ alkyls;

Further, $R_1$ is selected from the aryls substituted by $n_1$ $R_{11}$ groups;

$R_2$ is selected from the aryls substituted by $n_1'R_{11}'$ groups;

Wherein, $n_1$ and $n_1'$ are independently of each other selected from an integer of 0-5, and $R_{11}$ and $R_{11}'$ are independently of each other selected from the group consisting of deuterium, $C_{1-3}$ alkyls, methoxy, halogen, nitro, cyano, hydroxyl, carboxyl, amino, thiol, and ester group.

Further, $L_1$ is selected from substituted or unsubstituted $C_{2-14}$ alkylenyl;

Wherein, the main chain of said alkylenyl contains 0-3 heteroatoms, and said heteroatoms are selected from O, S, and $NR_{12}$, in which said $R_{12}$ is selected from hydrogen, deuterium, and $C_{1-2}$ alkyl; said substituent is deuterium, $C_{1-2}$ alkyl, and $C_{1-2}$ alkoxy;

When the dashed line in formula I is none, $L_2$ is selected from hydrogen, deuterium, and substituted or unsubstituted $C_{1-8}$ alkyl, in which said substituent is deuterium and $C_{1-2}$ alkyl; When the dashed line in formula I is a bond, $L_2$ is selected from substituted or unsubstituted $C_{2-6}$ alkylenyl, in which the substituent is deuterium, $C_{1-2}$ alkyl, and $C_{1-2}$ alkoxy.

Further, $L_1$ is selected from substituted or unsubstituted $C_{2-14}$ alkylenyl;

Wherein, the main chain of said alkylenyl contains 0-2 heteroatoms, and said heteroatoms are selected from O, S, and $NR_{12}$, in which said $R_{12}$ is selected from hydrogen and deuterium; said substituent is deuterium and $C_{1-2}$ alkyl;

When the dashed line in formula I is none, $L_2$ is selected from hydrogen, deuterium, and $C_{1-8}$ alkyl;

When the dashed line in formula I is a bond, $L_2$ is selected from substituted or unsubstituted $C_{2-6}$ alkylenyl, in which the substituent is deuterium, methyl, and methoxyl.

Further, said compound has a structure of formula II:

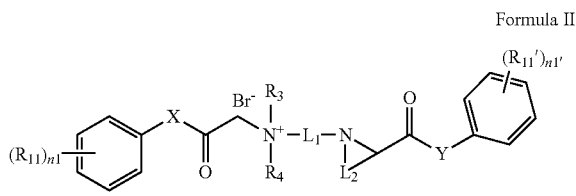

Formula II

In which,

X and Y are each independently selected from O and $NR_{10}$, in which $R_{10}$ is selected from H, deuterium or $C_4$ alkyl;

$R_{11}$ and $R_{11}'$ are independently of each other selected from the group consisting of deuterium, $C_{1-3}$ alkyls, methoxyl, halogen, nitro, cyano, hydroxyl, carboxyl, amino, thiol, and ester group;

$n_1$ and $n_1'$ are independently of each other selected from an integer of 2-3;

$L_1$ is selected from $C_{3-14}$ alkylenyl;

Wherein, the main chain of said alkylenyl contains 0-2 heteroatoms, and said heteroatoms are selected from O, S, and NR$_{12}$, in which said R$_{12}$ is selected from hydrogen and deuterium;

L$_2$ is selected from substituted or unsubstituted C$_{2-6}$ alkylenyl, in which said substituent is methyl and methoxyl.

Further, said compound has a structure of formula III:

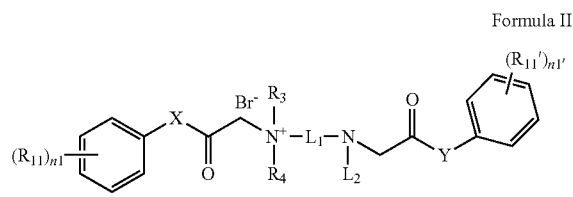

Formula III

In which,

X and Y are each independently selected from O, S, and NR$_{10}$, in which R$_{10}$ is selected from H, deuterium or C$_4$ alkyl;

R$_{11}$ and R$_{11}$' are independently of each other selected from the group consisting of deuterium, C$_1$ alkyl, methoxyl, and halogen;

n$_1$ and n$_1$' are independently of each other selected from an integer of 2-5;

L$_1$ is selected from C$_{2-10}$ alkylenyl;

Wherein, the main chain of said alkylenyl contains 0-2 heteroatoms, and said heteroatoms are selected from O, S, and NR$_{12}$, in which said R$_{12}$ is selected from hydrogen and deuterium;

L$_2$ is selected from H, deuterium, and C$_{1-8}$ alkylenyl;

The present invention further provides a method for preparing compound mentioned above, or pharmaceutically acceptable salts thereof, or stereoisomers thereof, or solvates thereof, or prodrugs thereof, or metabolites thereof, characterized in that the method includes the following steps:

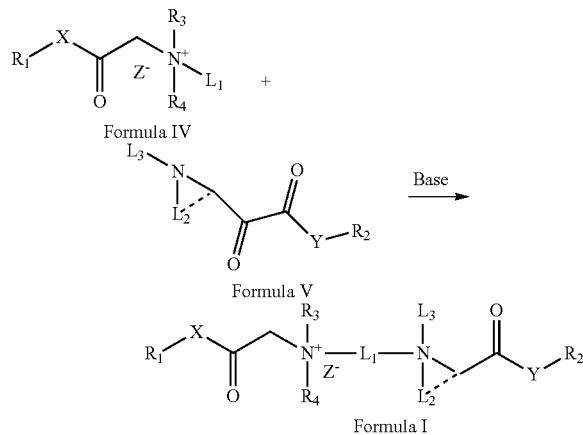

The quaternary ammonium compound of formula IV reacts with the amine compound formula V in the presence of a base, to obtain the target compound of formula I.

Further, said organic base is triethylamine or 1,8-diazabicycloundec-7-ene.

Further, said reaction is carried out in a polar protic solvent.

Further, said solvent is an alcohol, and preferably, the solvent is methanol or ethanol.

The present invention further provides the use of compound mentioned above, or pharmaceutically acceptable salts thereof, or stereoisomers thereof, or solvates thereof, or prodrugs thereof, or metabolites thereof in the preparation of local anesthetic drugs.

Further, said local anesthetic drug makes the block time of sensory nerve be longer than that of motor nerve.

Further, said local anesthesia is long-acting local anesthesia and/or selective local anesthesia.

Further, said local anesthesia lasts more than 24 hours.

The present invention further provides a drug, which is prepared using compound mentioned above, or pharmaceutically acceptable salts thereof, or stereoisomers thereof, or solvates thereof, or prodrugs thereof, or metabolites thereof, with the addition of pharmaceutically acceptable adjuvents.

The compounds and derivatives provided in the present invention can be named according to IUPAC (International Union of Pure and Applied Chemistry) or CAS (Chemical Abstracting Service, Columbus, Ohio) naming system.

For the definition of term used in the present invention: unless otherwise specified, the initial definition provided for the group or the term herein is applicable to those in the whole specification; for terms not specifically defined herein, according to the disclosure content and the context, the term should have the meaning commonly given by those skilled in the field.

"Substitution" means that the hydrogen in a molecule is substituted by other different atoms or molecules.

Halogen is fluorine, chlorine, bromine or iodine.

"Alkyls" is a hydrocarbon group formed by losing one hydrogen in an alkane molecule, such as methyl —CH$_3$, ethyl —CH$_3$CH$_2$, etc. "C$_{1-4}$ alkyls" denotes a straight or branched hydrocarbon chain containing 1-4 carbon atoms.

"Alkylenyls" denotes the hydrocarbon group formed by losing two hydrogens in the alkane molecule, such as methylene —CH$_2$—, ethylidene —CH$_2$CH$_2$—, etc. "C$_{1-4}$ alkylenyls" denotes a straight or branched hydrocarbon chain containing 1-4 carbon atoms.

"Substituted or unsubstituted C$_{1-12}$ alkyls" denotes C$_{1-12}$ alkyls that can be substituted or not be substituted.

"L$_1$ is selected from substituted or unsubstituted C$_{1-12}$ alkylenyl; wherein, the main chain of said alkylenyl contains 0-4 heteroatoms" means a straight or branched hydrocarbon chain containing 1-12 carbon atoms; said hydrocarbon chain can be substituted or unsubstituted; the main chain of said hydrocarbon contains heteroatoms that are 0, S, and substituted N atoms.

"When the dashed line in formula I is none" means that the dashed line in formula I does not exist; that is, at this time L$_2$ does not take part in the formation of the ring, and L$_2$ is selected from hydrogen, deuterium, substituted or unsubstituted C$_{1-8}$ alkyl, and substituted or unsubstituted C$_{1-8}$ alkoxyl, in which said substituent is deuterium, C$_{1-4}$ alkyl, C$_{1-4}$ alkoxyl, and halogen;

"When the dashed line in formula I is a bond" means that L$_2$ forms a ring with N atom and the carbon atom linkage with the carbonyl, and at this time L$_2$ is selected from substituted or unsubstituted C$_{1-8}$ alkylenyl, in which the substituent is deuterium, C$_{1-4}$ alkyl, C$_{1-4}$ alkoxy, and halogen; meanwhile, compound of formula I has a structure of formula I':

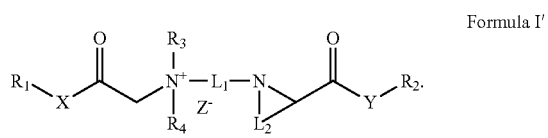

Formula I'

"Aryls" denote all-carbon monocyclic or fused polycyclic (i.e. ring sharing adjacent carbon atom pairs) groups with conjugated π electron system, such as phenyl and naphthyl. Said aryl ring can be fused to other cyclic groups (including saturated and unsaturated rings), but can not contain hetero atoms such as nitrogen, oxygen, or sulfur. At the same time, the point connecting with the parent must be on the carbon in the ring having the conjugated π electron system. Aryls can be substituted or unsubstituted, i.e. aryls can be substituted by 0-4 deuterium, $C_{1-4}$ alkyl, $C_{1-4}$ alkoxy, halogen, nitro, cyano, hydroxyl, carboxyl, and amino.

The term "pharmaceutically acceptable salt" denotes the salt formed by the compound of the present invention and pharmaceutically acceptable inorganic and organic acids, which is suitable for contacting the tissue of the object (e.g. human) without undue side effects. Among them, the preferred inorganic acids include (but not limited to) hydrochloric acid, hydrobromic acid, phosphoric acid, nitric acid, sulfuric acid; the preferred organic acids include (but not limited to) formic acid, acetic acid, propionic acid, succinic acid, naphthalene disulfonic acid (1,5), asiatic acid, oxalic acid, tartaric acid, lactic acid, salicylic acid, benzoic acid, valeric acid, diethylacetic acid, malonic acid, succinic acid, fumaric acid, pimelic acid, adipic acid, maleic acid, malic acid, sulfamic acid, phenylpropionic acid, gluconic acid, ascorbic acid, niacin, isoniacin, methanesulfonic acid, p-toluenesulfonic acid, citric acid, and amino acids.

The term "solvate" denotes the solvate formed by the compound of the present invention and pharmaceutically acceptable solvents, in which the pharmaceutically acceptable solvent includes (but not limited to) water, ethanol, methanol, isopropanol, propylene glycol, tetrahydrofuran, and dichloromethane.

The term "pharmaceutically acceptable stereoisomer" means that the chiral carbon atom involved in the compound of the present invention may be R-configuration, S-configuration, or a combination thereof.

The present invention provides a new class of quaternary ammonium compounds with novel structures, as well as the preparative method and the use thereof. The compound has a fast onset of action and a long-time local anesthetic effect after a single administration. The block time of sensory nerve is longer than that of motor nerve, and the compound has both long-acting and selective local anesthetic effect, that significantly reduced the side effects of QX314, QX314 composition, and the quaternary ammonium compound with surfactant structure characteristics. That is, the compound of formula I according to the present invention and its pharmaceutically acceptable salts can be used to prepare safe drugs with long-acting and selective local anesthesia, which has the advantages of long-time local anesthetic action, good local anesthetic selectivity, less nerve damage, and high safety.

Obviously, based on above content of the present invention, according to the common technical knowledge and the conventional means in the field, without department from above basic technical spirits, other various modifications, alternations or changes can further be made.

By following specific examples of said embodiments, above content of the present invention is further illustrated. But it should not be construed that the scope of above subject of the present invention is limited to following examples. The techniques realized based on above content of the present invention are all within the scope of the present invention.

EXAMPLES

The starting materials and equipment used in the specific examples of the present invention are all known products and can be obtained by purchasing commercially available items.

Example 1 Preparation of Compound of the Present Invention

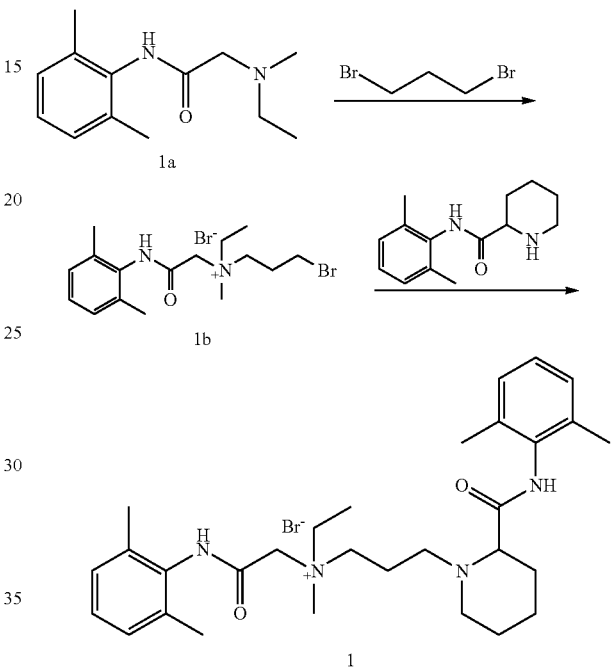

Compound 1a (10.0 g, 45.39 mmol) was dissolved in 1,3-dibromopropane (15 mL), and the mixture was heated to 75° C. and reacted for 40 h. The reaction was monitored by TLC (DCM:MeOH=10:1, Rf=0.3). A suitable amount of ethyl acetate was added to form a viscous syrupy substance. The supernatant was poured out, to obtain the residue of 15 g crude product, which was dissolved in 30 mL methanol and mixed with silica gel. After dry loading, silica gel column chromatography was used for purification, with eluent: $CH_2Cl_2$:MeOH=10:1. The eluent was collected and concentrated to obtain 7.0 g crude product. The resultant product was recrystallized in ethyl acetate and dichloromethane, to prepare 6.6 g off-white solid powder (intermediate 1b) with a yield of 34.4%, which was used in the next reaction.

Intermediate 1b (1.00 g, 2.37 mmol) prepared above and N-(2,6-dimethylphenyl)-2-piperidinecarboxamide (0.604 g, 2.61 mmol, CAS: 15883-20-2) were dissolved in 10 mL ethanol, to which was added DIPEA (0.99 g, 0.78 mL, 4.74 mmol). The mixture was warmed to 80° C. and kept for 40 hours. Then, the solvent was evaporated, and the crude product was purified by silica gel column chromatography, using eluent: $CH_2Cl_2$:MeOH=10:1. The eluate was collected and concentrated to obtain 600 mg white solid (1). Yield: 44.15%. $^1$H NMR (300 MHz, $CDCl_3$) δ (ppm): 10.35 (s, 1H), 7.84 (s, 1H), 7.11-7.01 (m, 6H), 4.89 (s, 2H), 3.80-3.45 (m, 6H), 3.20 (s, 3H), 2.71-2.57 (m, 2H), 2.28-2.17 (m, 14H), 2.02 (m, 1H), 1.90-1.63 (m, 6H), 1.60-1.27 (m, 3H).

Example 2 Preparation of Compound of the Present Invention

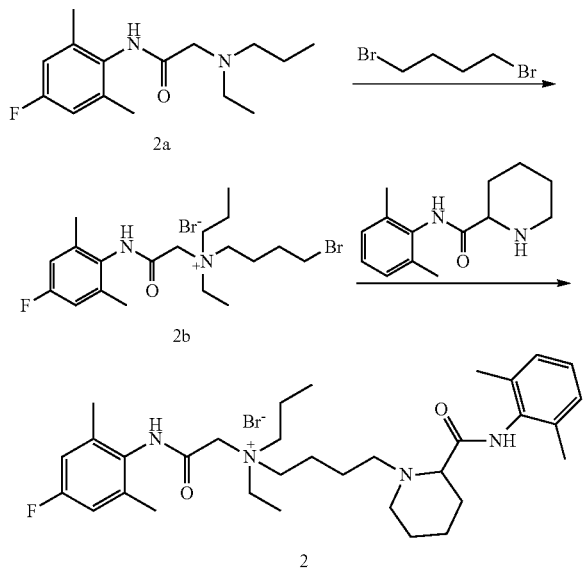

Compound 2a (10.0 g, 40.32 mmol) was dissolved in 1,3-dibromobutane (20 mL), and the mixture was heated to 75° C. and reacted for 24 h. The reaction was monitored by TLC (DCM:MeOH=10:1, Rf=0.3). A suitable amount of ethyl acetate was added, then the reaction solution solidified to produce white solids, and 16.0 g crude product was filtered out as white solid, that was purified by silica gel column chromatography, using eluent: $CH_2Cl_2$:MeOH=20:1. The eluent was collected and concentrated to obtain 5.9 g white solid (intermediate 2b), with a yield of 31.5%, which was used in the next reaction.

Intermediate 2b (1.0 g, 2.16 mmol) prepared above and N-(2,6-dimethylphenyl)-2-piperidinecarboxamide (0.55 g, 2.37 mmol, CAS: 15883-20-2) were dissolved in 15 mL ethanol, to which was added DIPEA (0.53 g, 0.68 mL, 4.12 mmol). The mixture was allowed to react for 10 days at the temperature of 30° C. Then, the solvent was evaporated, and the crude product was purified by silica gel column chromatography, using eluent: $CH_2Cl_2$:MeOH=10:1. The eluate was collected and concentrated to obtain 995 mg white powder solid (2). Yield: 75.1%. $^1$H NMR (300 MHz, $CDCl_3$) δ (ppm): 9.79 (s, 1H), 7.60 (s, 1H), 7.02-6.90 (m, 5H), 4.33 (s, 2H), 3.63-3.41 (m, 6H), 3.25-3.01 (m, 2H), 2.94 (s, 2H), 2.08 (s, 6H), 2.07 (s, 6H), 1.89-1.74 (m, 12H), 1.60-1.40 (m, 1H), 1.40-1.20 (m, 6H).

Example 3 Preparation of Compound of the Present Invention

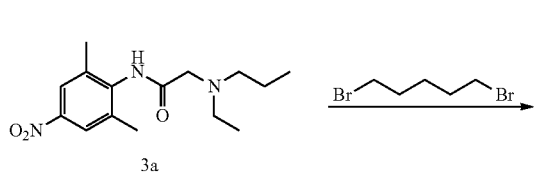

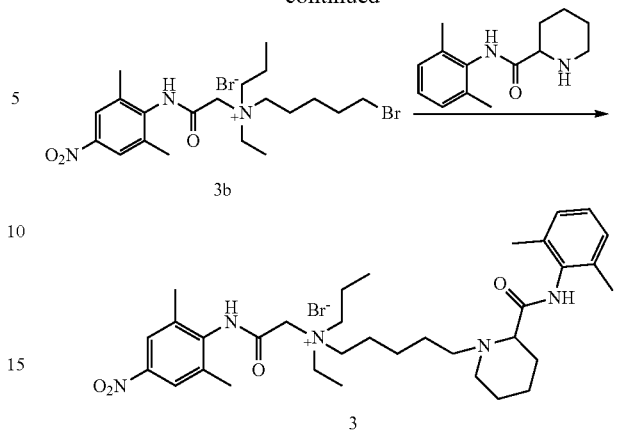

Compound 3a (2.0 g, 8.06 mmol) was dissolved in 1,5-dibromopentane (4 mL), and the mixture was heated to 70° C. and reacted for 24 h. The reaction was monitored by TLC (DCM:MeOH=20:1, Rf=0.3). A suitable amount of ethyl acetate was added, then the reaction solution solidified to produce white solids, and 16.0 g crude product was filtered out as white solid, that was purified by silica gel column chromatography, using eluent: $CH_2Cl_2$:MeOH=20:1. The eluent was collected and concentrated to obtain 1.8 g white powder solid (intermediate 3b), with a yield of 46.7%, which was used in the next reaction.

Intermediate 3b (1.8 g, 3.77 mmol) prepared above and N-(2,6-dimethylphenyl)-2-piperidinecarboxamide (0.96 g, 4.14 mmol, CAS: 15883-20-2) were dissolved in the solvent mixture of 30 mL ethanol and 5 mL methanol, to which was added DIPEA (0.97 g, 1.24 mL, 7.54 mmol). The mixture was allowed to react for 18 days at the temperature of 30° C. After completion of the reaction, the crude product was purified by silica gel column chromatography, using eluent: $CH_2Cl_2$:MeOH=10:1. The eluate was collected and concentrated to obtain 500 mg white powder solid (3). Yield: 20.1%. $^1$H NMR (300 MHz, $CDCl_3$) δ (ppm): 10.24 (s, 1H), 8.39 (s, 1H), 7.05-6.87 (m, 5H), 4.68 (s, 2H), 3.60-3.50 (m, 6H), 3.30-3.05 (m, 2H), 2.90-2.70 (m, 1H), 2.35 (s, 1H), 2.17-2.14 (m, 12H), 2.05-1.55 (m, 10H), 1.49-1.31 (m, 11H).

Example 4 Preparation of Compound of the Present Invention

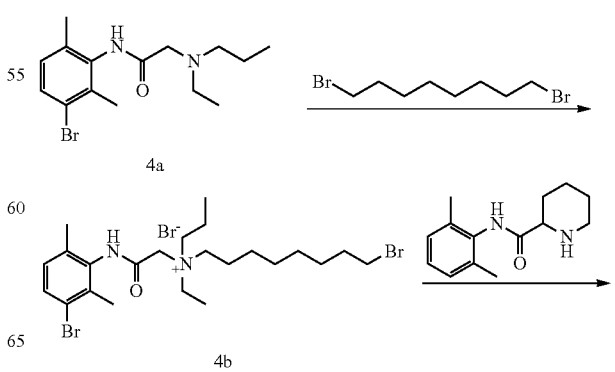

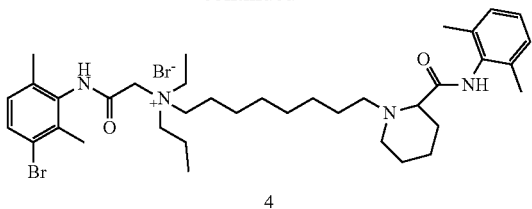

4

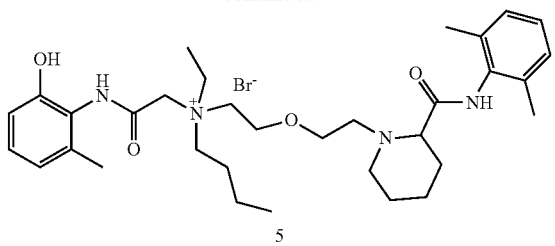

5

Compound 4a (10.0 g, 40.3 mmol) was dissolved in 1,8-dibromooctane (15 mL), and the mixture was heated to 75° C. and reacted for 40 h. The reaction was monitored by TLC (DCM:MeOH=10:1). A suitable amount of ethyl acetate was added to form a viscous syrupy substance. The supernatant was poured out, and the residual solid was dissolved, mixed with silica gel, and purified by silica gel column chromatography, with eluent: CH$_2$Cl$_2$:MeOH=10:1. The eluent was collected and concentrated to obtain 7.4 g crude product. The resultant product was recrystallized in ethyl acetate and dichloromethane, to prepare 6.9 g off-white solid powder (intermediate 4b), which was directly used in the next reaction.

Intermediate 4b (1.00 g, 1.92 mmol) prepared above and N-(2,6-dimethylphenyl)-2-piperidinecarboxamide (498 mg, 2.11 mmol, CAS: 15883-20-2) were dissolved in 10 mL ethanol, to which was added DIPEA (0.63 mL, 3.84 mmol). The mixture was warmed to 80° C. and kept for 40 hours. Then, the solvent was evaporated, and the crude product was purified by silica gel column chromatography, using eluent: CH$_2$Cl$_2$:MeOH=10:1. The eluate was collected and concentrated to obtain 600 mg white solid (4). Yield: 46.6%. $^1$H NMR (300 MHz, CDCl$_3$) δ (ppm): 10.50 (s, 1H), 8.13 (s, 1H), 7.11-7.01 (m, 5H), 4.88 (s, 2H), 3.64-3.61 (d, J=7.02 Hz, 4H), 3.48 (s, 2H), 2.96 (s, 1H), 2.86-2.79 (m, 2H), 2.27 (s, 6H), 2.23 (s, 6H), 2.17-1.96 (m, 4H), 1.76 (s, 10H), 1.60-1.42 (m, 14H).

Compound 5a (1.0 g, 3.8 mmol) was dissolved in 1 mL bis(2-bromoethyl) ether and slowly added dropwise to 1.5 mL bis(2-bromoethyl) ether, and the mixture was heated to 70° C. and reacted. The reaction was monitored by TLC (DCM:MeOH=10:1). After completion of the reaction, the solvent was evaporated, and the crude product was purified by silica gel column chromatography, using eluent: CH$_2$Cl$_2$:MeOH=20:1. The eluent was collected and concentrated to obtain 1.3 g brown compound (intermediate 5b), with a yield of 69.0%, which was used in the next reaction. Intermediate 5b (1.3 g, 2.6 mmol) prepared above and N-(2,6-dimethylphenyl)-2-piperidinecarboxamide (0.67 g, 2.89 mmol, CAS: 15883-20-2) were dissolved in 15 mL ethanol, to which was added DIPEA (0.86 g, 5.2 mmol). The mixture was allowed to react for 13 days at the temperature of 30° C., and the reaction was detected by TLC (DCM:MeOH=10:1). After completion of the reaction, the solvent was evaporated, and the crude product was purified by silica gel column chromatography, using eluent: CH$_2$Cl$_2$:MeOH=10:1. The eluate was collected and concentrated to obtain 500 mg white solid (5). Yield: 29.4%. $^1$H NMR (300 MHz, CDCl$_3$) δ (ppm): 10.09 (s, 1H), 9.81 (s, m), 8.69 (s, 1H), 7.06-6.90 (m, 6H), 4.73 (s, 2H), 4.67-3.97 (d, J=4.05 Hz, 2H), 3.85-3.63 (m, 8H), 3.28-3.16 (m, 2H), 3.07-2.95 (m, 1H), 2.65-2.56 (m, 1H), 2.30-1.95 (m, 13H), 1.80-1.60 (m, 4H), 1.60-1.12 (m, 11H).

Example 5 Preparation of Compound of the Present Invention

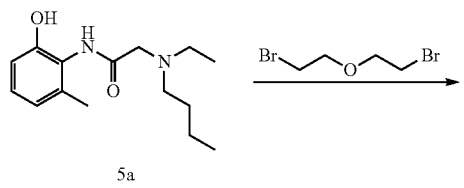

5a

Example 6 Preparation of Compound of the Present Invention

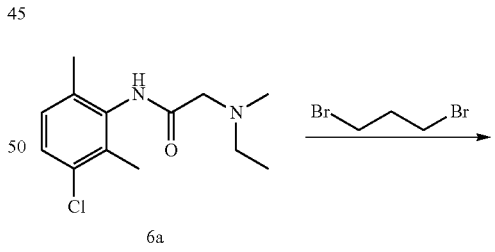

6a

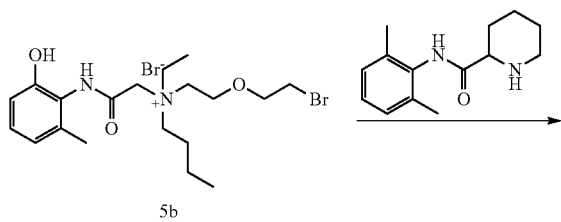

5b

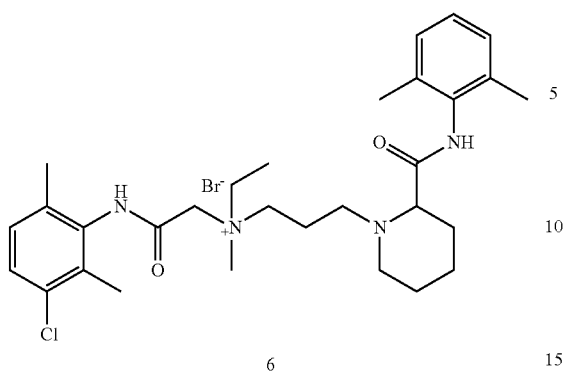

6

Compound 6a (10.0 g, 39.4 mmol) was dissolved in 1,3-dibromopropane (15 mL), and the mixture was heated to 75° C. and reacted for 40 h. The reaction was monitored by TLC (DCM:MeOH=10:1, Rf=0.3). A suitable amount of ethyl acetate was added to form a viscous syrupy substance. The supernatant was poured out, to obtain the residue of 14 g crude product, which was dissolved in 30 mL methanol and mixed with silica gel. After dry loading, silica gel column chromatography was used for purification, with eluent: $CH_2Cl_2$:MeOH=10:1. The eluent was collected and concentrated to obtain 8.0 g crude product. The resultant product was recrystallized in ethyl acetate and dichloromethane, to prepare 7.6 g off-white solid powder (intermediate 6b) with a yield of 42.3%, which was used in the next reaction.

Intermediate 1b (1.00 g, 2.19 mmol) prepared above and N-(2,6-dimethylphenyl)-2-piperidinecarboxamide (0.559 g, 2.4 mmol, CAS: 15883-20-2) were dissolved in 10 mL ethanol, to which was added DIPEA (0.57 g, 0.72 mL, 4.38 mmol). The mixture was heated to 80° C. and kept for 40 hours. Then, the solvent was evaporated, and the crude product was purified by silica gel column chromatography, using eluent: $CH_2Cl_2$:MeOH=10:1. The eluate was collected and concentrated to obtain 500 mg white solid (6). Yield: 37.6%. $^1$H NMR (300 MHz, $CDCl_3$) δ (ppm): 10.35 (s, 1H), 7.84 (s, 1H), 7.11-7.01 (m, 5H), 4.89 (s, 2H), 3.80-3.45 (m, 6H), 3.20 (s, 3H), 2.71-2.57 (m, 2H), 2.28-2.17 (m, 14H), 2.02 (m, 1H), 1.90-1.63 (m, 6H), 1.60-1.27 (m, 3H).

Example 7 Preparation of Compound of the Present Invention

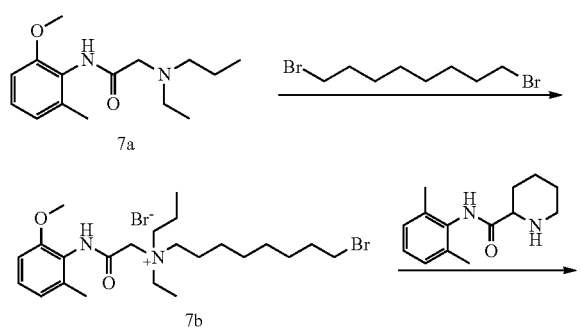

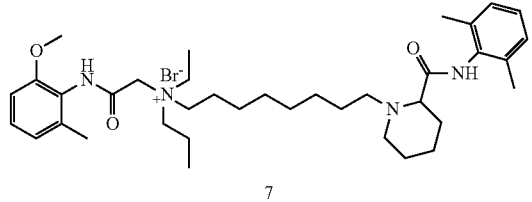

7

Compound 7a (10.0 g, 37.88 mmol) was dissolved in 1,8-dibromooctane (15 mL), and the mixture was heated to 75° C. and reacted for 40 h. The reaction was monitored by TLC (DCM:MeOH=10:1). A suitable amount of ethyl acetate was added to form a viscous syrupy substance. The supernatant was poured out, and the residual solid was dissolved, mixed with silica gel, and purified by silica gel column chromatography, with eluent: $CH_2Cl_2$:MeOH=10:1. The eluent was collected and concentrated to obtain 8.4 g crude product. The resultant product was recrystallized in ethyl acetate and dichloromethane, to prepare 7.4 g off-white solid powder (intermediate 7b), which was directly used in the next reaction.

Intermediate 7b (1.00 g, 1.87 mmol) prepared above and N-(2,6-dimethylphenyl)-2-piperidinecarboxamide (475 mg, 2.05 mmol, CAS: 15883-20-2) were dissolved in 10 mL ethanol, to which was added DIPEA (0.62 mL, 3.74 mmol). The mixture was heated to 80° C. and kept for 40 hours. Then, the solvent was evaporated, and the crude product was purified by silica gel column chromatography, using eluent: $CH_2Cl_2$:MeOH=10:1. The eluate was collected and concentrated to obtain 500 mg white solid (7). Yield: 38.8%. 41 NMR (300 MHz, $CDCl_3$) δ (ppm): 10.50 (s, 1H), 8.13 (s, 1H), 7.11-7.01 (m, 6H), 4.88 (s, 2H), 3.64-3.61 (d, J=7.02 Hz, 4H), 3.86 (s, 3H), 3.48 (s, 2H), 2.96 (s, 1H), 2.86-2.79 (m, 2H), 2.27 (s, 6H), 2.23 (s, 3H), 2.17-1.96 (m, 4H), 1.76 (s, 10H), 1.60-1.42 (m, 14H).

Example 8 Preparation of Compound of the Present Invention

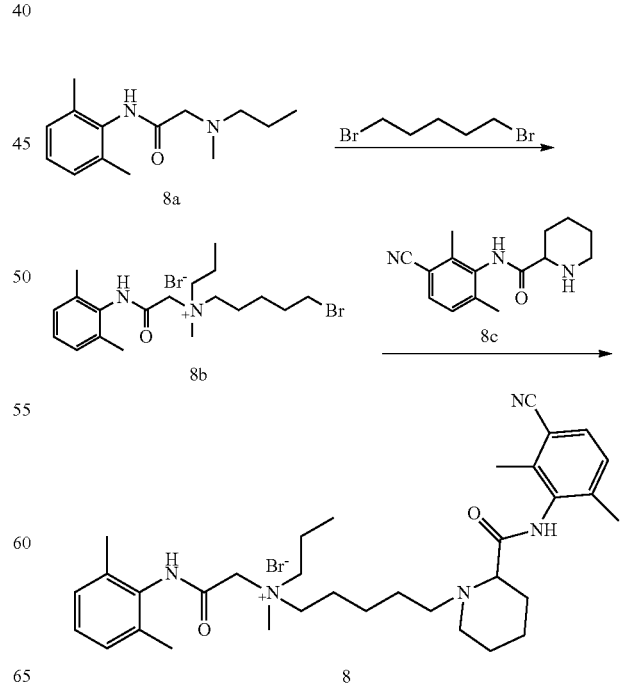

Compound 8a (2.0 g, 8.54 mmol) was dissolved in 1,5-dibromopentane (4 mL), and the mixture was heated to 70° C. and reacted for 24 h. The reaction was monitored by TLC (DCM:MeOH=20:1, Rf=0.3). A suitable amount of ethyl acetate was added, then the reaction solution solidified to produce white solids, and 1.8 g crude product was filtered out as white solid, that was purified by silica gel column chromatography, using eluent: $CH_2Cl_2$:MeOH=20:1. The eluent was collected and concentrated to obtain 1.6 g white powder solid (intermediate 8b), with a yield of 39.2%, which was used in the next reaction.

Intermediates 8b (1.5 g, 3.23 mmol) and 8c (0.91 g, 3.55 mmol) were dissolved in the solvent mixture of 30 mL ethanol and 5 mL methanol, to which was added DIPEA (0.83 g, 1.06 mL, 6.46 mmol). The mixture was allowed to react for 18 days at the temperature of 30° C. After completion of the reaction, the crude product was purified by silica gel column chromatography, using eluent: $CH_2Cl_2$:MeOH=10:1. The eluate was collected and concentrated to obtain 600 mg white powder solid (8). Yield: 29.0%. $^1$H NMR (300 MHz, $CDCl_3$) δ (ppm): 10.24 (s, 1H), 8.39 (s, 1H), 7.05-6.87 (m, 5H), 4.68 (s, 2H), 3.60-3.50 (m, 6H), 3.33 (s, 3H), 2.90-2.70 (m, 1H), 2.35 (s, 1H), 2.17-2.14 (m, 12H), 2.05-1.55 (m, 10H), 1.49-1.31 (m, 11H).

Example 9 Preparation of Compound of the Present Invention

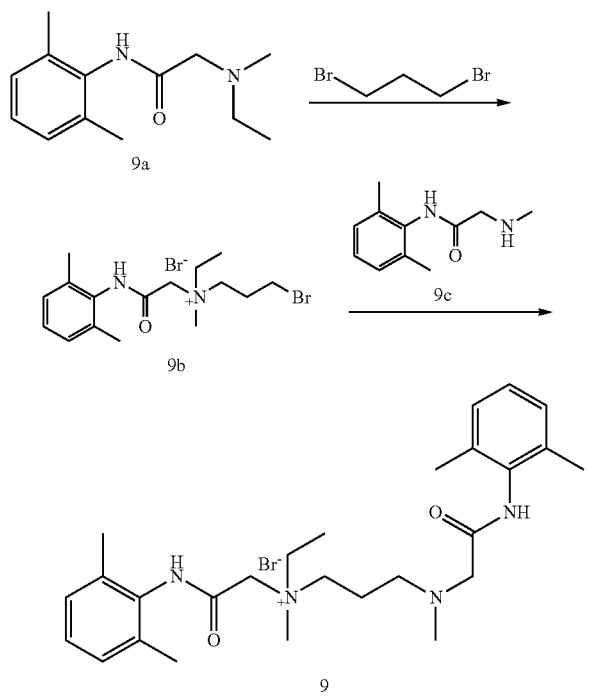

Compound 9a (10.0 g, 45.45 mmol) was dissolved in 1,3-dibromopropane (15 mL), and the mixture was heated to 75° C. and reacted for 40 h. The reaction was monitored by TLC (DCM:MeOH=10:1, Rf=0.3). A suitable amount of ethyl acetate was added to form a viscous syrupy substance. The supernatant was poured out, to obtain the residue of 14 g crude product, which was dissolved in 30 mL methanol and mixed with silica gel. After dry loading, silica gel column chromatography was used for purification, with eluent: $CH_2Cl_2$:MeOH=10:1. The eluent was collected and concentrated to obtain 8.0 g crude product. The resultant product was recrystallized in ethyl acetate and dichloromethane, to prepare 7.2 g off-white solid powder (intermediate 9b) with a yield of 37.5%, which was used in the next reaction.

Intermediates 9b (1.00 g, 2.37 mmol) and 9c (0.504 g, 2.61 mmol) prepared above were dissolved in 10 mL ethanol, to which was added DIPEA (0.99 g, 0.78 mL, 4.74 mmol). The mixture was heated to 80° C. and kept for 40 hours. Then, the solvent was evaporated, and the crude product was purified by silica gel column chromatography, using eluent: $CH_2Cl_2$:MeOH=10:1. The eluate was collected and concentrated to obtain 500 mg white solid (9). Yield: 39.6%. $^1$H NMR (300 MHz, $CDCl_3$) δ (ppm): 10.35 (s, 1H), 7.84 (s, 1H), 7.11-7.01 (m, 6H), 4.89 (s, 2H), 3.80-3.45 (m, 6H), 3.20 (s, 3H), 2.71-2.57 (m, 2H), 2.32 (s, 3H) 2.28-2.17 (m, 11H), 2.02 (m, 1H), 1.90-1.63 (m, 2H), 1.60-1.27 (m, 3H).

Example 10 Preparation of Compound of the Present Invention

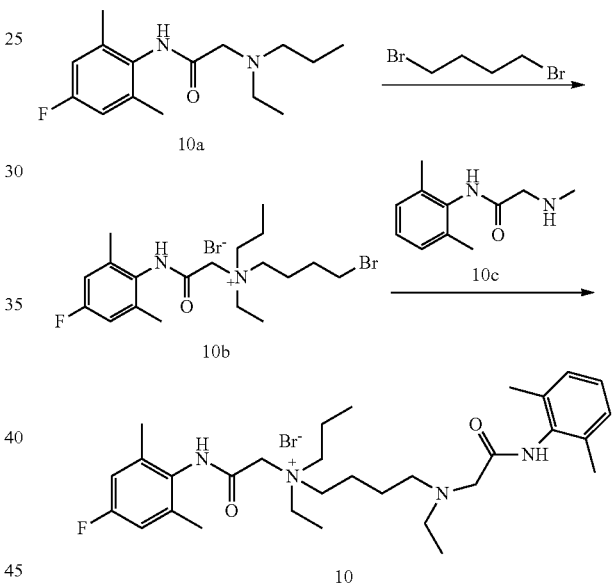

Compound 10a (10.0 g, 37.59 mmol) was dissolved in 1,3-dibromobutane (20 mL), and the mixture was heated to 75° C. and reacted for 24 h. The reaction was monitored by TLC (DCM:MeOH=10:1, Rf=0.3). A suitable amount of ethyl acetate was added, then the reaction solution solidified to produce white solids, and 15.0 g crude product was filtered out as white solid, that was purified by silica gel column chromatography, using eluent: $CH_2Cl_2$:MeOH=20:1. The eluent was collected and concentrated to obtain 6.5 g white solid (intermediate 10b), with a yield of 35.9%, which was used in the next reaction.

Intermediates 10b (1.0 g, 2.07 mmol) and 10c (0.47 g, 2.28 mmol) prepared above were dissolved in 15 mL ethanol, to which was added DIPEA (0.54 g, 0.69 mL, 4.14 mmol). The mixture was allowed to react for 10 days at the temperature of 30° C. Then, the solvent was evaporated, and the crude product was purified by silica gel column chromatography, using eluent: $CH_2Cl_2$:MeOH=10:1. The eluate was collected and concentrated to obtain 900 mg white powder solid (10). Yield: 71.6%. $^1$H NMR (300 MHz, $CDCl_3$) δ (ppm): 9.79 (s, 1H), 7.60 (s, 1H), 7.02-6.90 (m, 5H), 4.33 (s, 2H), 3.26-3.06 (m, 6H), 2.64-2.42 (m, 4H), 2.10 (s, 6H), 2.09 (s, 6H), 1.89-1.74 (m, 8H), 1.40-1.20 (m, 9H).

Example 11 Preparation of Compound of the Present Invention

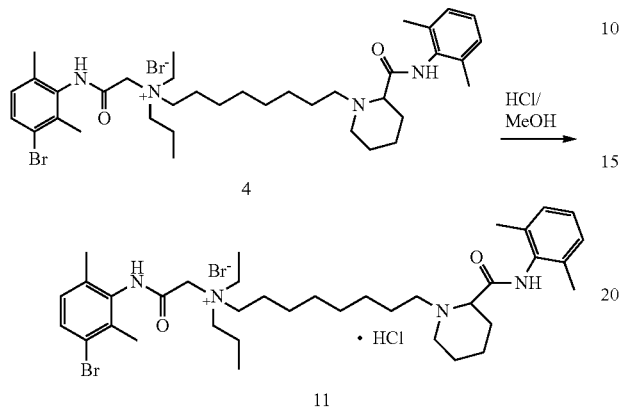

200 mg product obtained in Example 4 was dissolved in 10 mL dichloromethane, and an equal molar amount of hydrochloric acid-methanol solution at the concentration of 0.1 mol/L was added dropwise on an ice bath. The mixture was concentrated to dryness under reduced pressure. Then, the resultant product was dried in vacuo to obtain a pale yellow solid (11).

Example 12 Preparation of Compound of the Present Invention 200 mg product obtained in Example 10 was dissolved in 10 mL dichloromethane, to which was added 1 eq p-toluenesulfonic acid. The mixture was concentrated to dryness under reduced pressure. Then, the resultant product was dried in vacuo to obtain a pale yellow solid (12).

Example 13 Preparation of Compound of the Present Invention 200 mg product obtained in Example 8 was dissolved in 10 mL dichloromethane, to which was added 0.5 eq D-tartaric acid. The mixture was concentrated to dryness under reduced pressure. Then, the resultant product was dried in vacuo to obtain a pale yellow solid (13).

According to the preparative methods in above examples, compounds 14-77 in the following examples are obtained:

| Structure | Molecular formula and the molecular weight in MS |
|---|---|
| (14) | ESI[M⁺]: 493.4 |

| Structure | Molecular formula and the molecular weight in MS |
|---|---|
| 15 | ESI[M+]: 591.5 |
| 16 | ESI[M+]: 493.4 |
| 17 | ESI[M+]: 675.6 |
| 18 | ESI[M+]: 569.4 |
| 19 | ESI[M+]: 591.5 |

-continued
| Structure | Molecular formula and the molecular weight in MS |
|---|---|
| 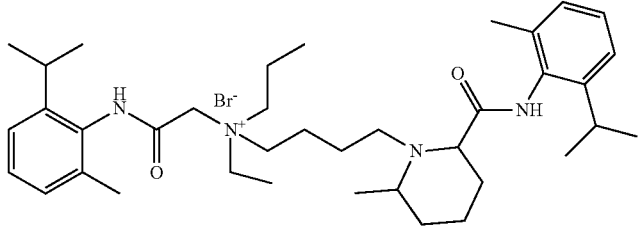<br>20 | ESI[M⁺]: 605.5 |
| 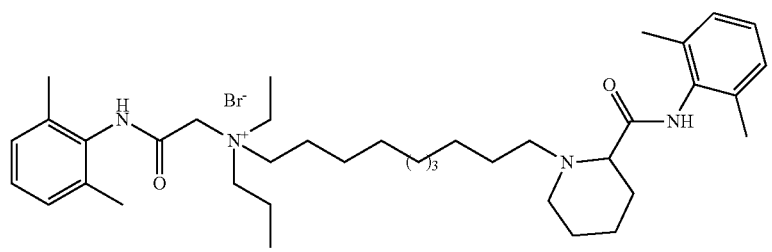<br>21 | ESI[M⁺]: 619.50 |
| 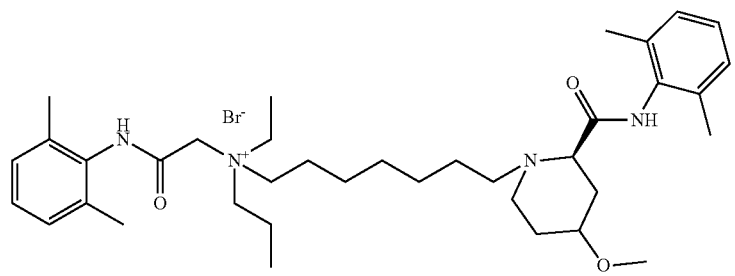<br>22 | ESI[M⁺]: 607.5 |
| 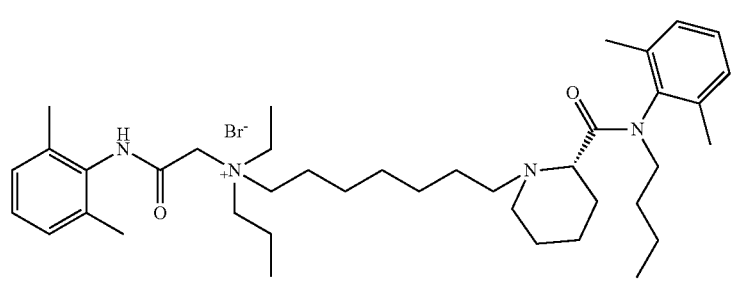<br>23 | ESI[M⁺]: 634.5 |
| 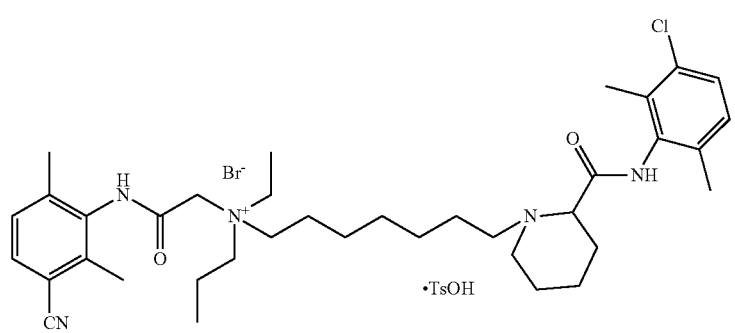<br>24 | ESI[M⁺]: 636.4 |

| Structure | Molecular formula and the molecular weight in MS |
|---|---|
| 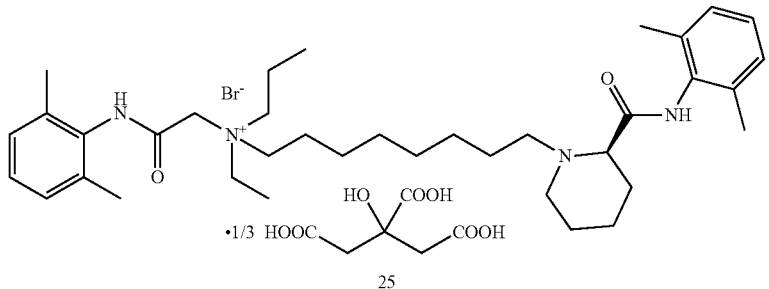<br>25 | ESI[M+]: 591.5 |
| 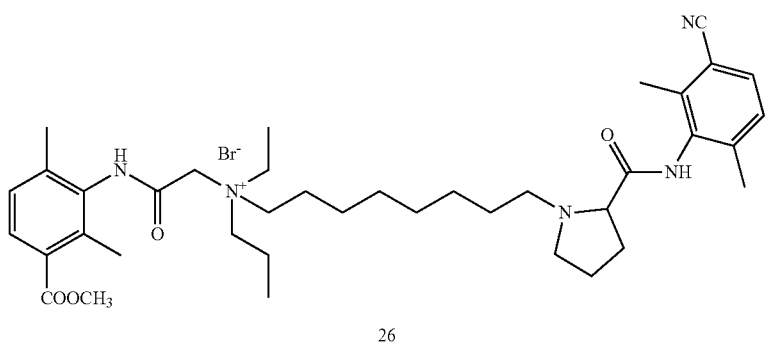 [SMILES: CCC[N+](CC)(CCCCCCCCN1CCCC1C(=O)Nc1c(C)ccc(C#N)c1C)CC(=O)Nc1c(C)ccc(C(=O)OC)c1C ; [Br-]]<br>26 | ESI[M+]: 660.4 |
| 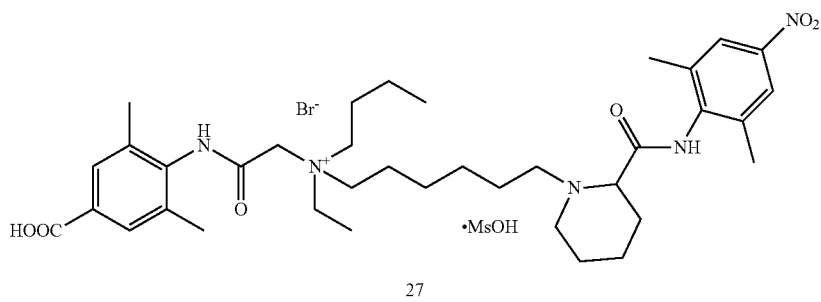 [SMILES: "·MsOH" ; CCCC[N+](CC)(CCCCCCN1CCCCC1C(=O)Nc1c(C)cc([N+](=O)[O-])cc1C)CC(=O)Nc1c(C)cc(C(=O)O)cc1C ; [Br-]]<br>27 | ESI[M+]: 666.4 |
| 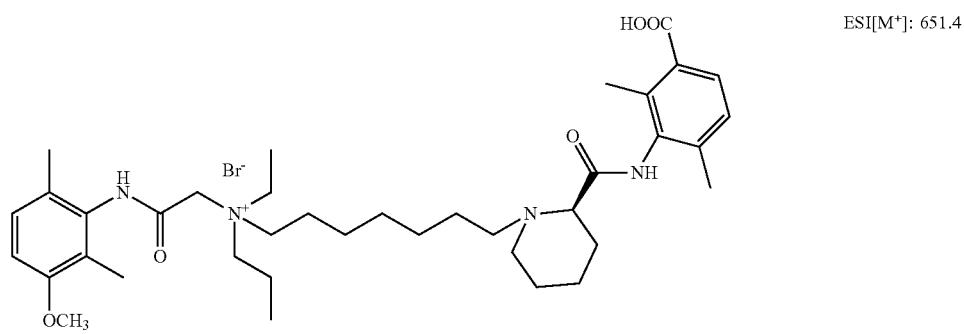<br>28 | ESI[M+]: 651.4 |

| Structure | Molecular formula and the molecular weight in MS |
|---|---|
| 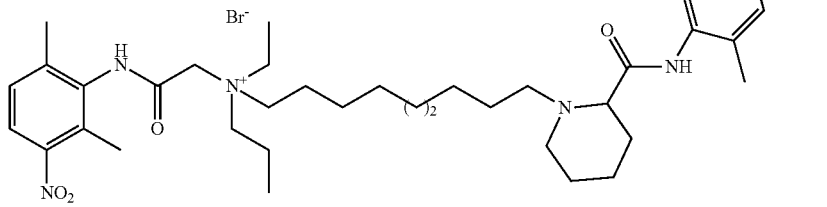 29 | ESI[M+]: 680.5 |
| 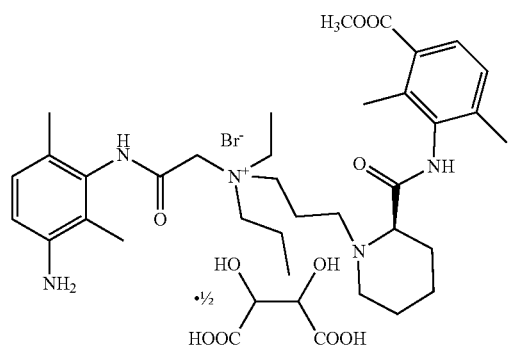 30 | ESI[M+]: 594.4 |
| 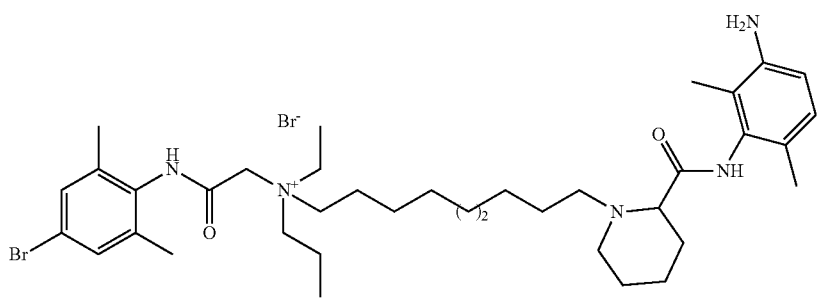 31 | ESI[M+]: 698.4 |
| 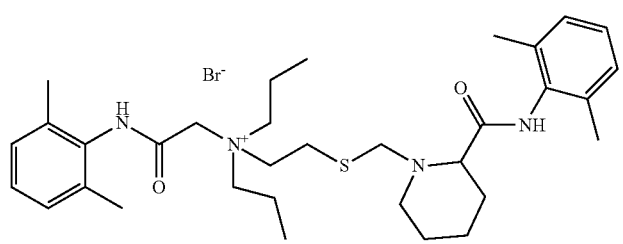 32 | ESI[M+]: 567.4 |

| Structure | Molecular formula and the molecular weight in MS |
|---|---|
| 33 | ESI[M⁺]: 623.5 |
| 34 | ESI[M⁺]: 565.4 |
| 35 | ESI[M⁺]: 565.4 |
| 36 | ESI[M⁺]: 535.4 |

-continued

| Structure | Molecular formula and the molecular weight in MS |
|---|---|
| 37 | ESI[M⁺]: 649.5 |
| 38 | ESI[M⁺]: 609.5 |
| 39 | ESI[M⁺]: 623.5 |
| 40 | ESI[M⁺]: 523.4 |
| 41 | ESI[M⁺]: 613.4 |

-continued
| Structure | Molecular formula and the molecular weight in MS |
|---|---|
| 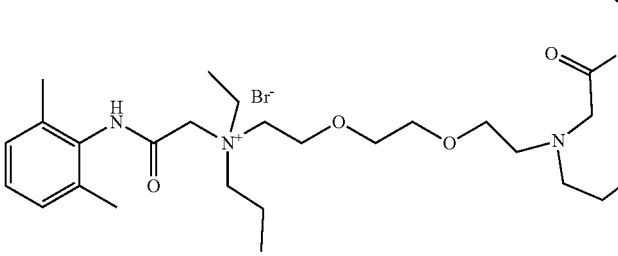 42 | ESI[M+]: 597.4 |
| 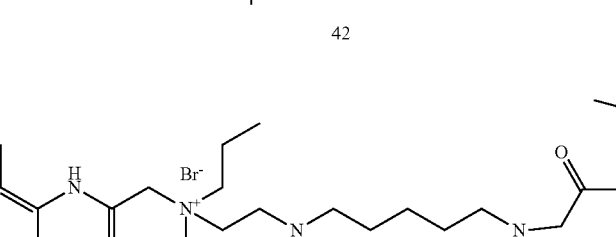 43 | ESI[M+]: 608.5 |
| 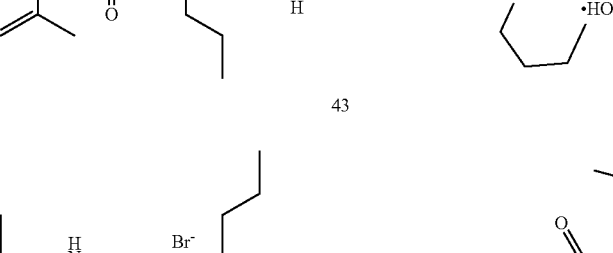 44 | ESI[M+]: 564.4 |
| 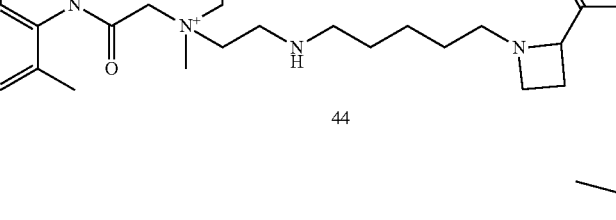 45 | ESI[M+]: 649.5 |
| 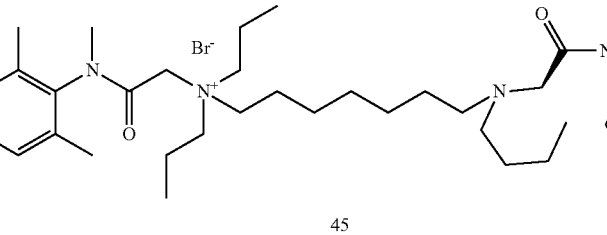 46 | ESI[M+]: 599.4 |

-continued

| Structure | Molecular formula and the molecular weight in MS |
|---|---|
| 47 | ESI[M⁺]: 651.5 |
| 48 | ESI[M⁺]: 641.5 |
| 49 | ESI[M⁺]: 580.5 |
| 50 | ESI[M⁺]: 555.4 |

-continued
| Structure | Molecular formula and the molecular weight in MS |
|---|---|
| 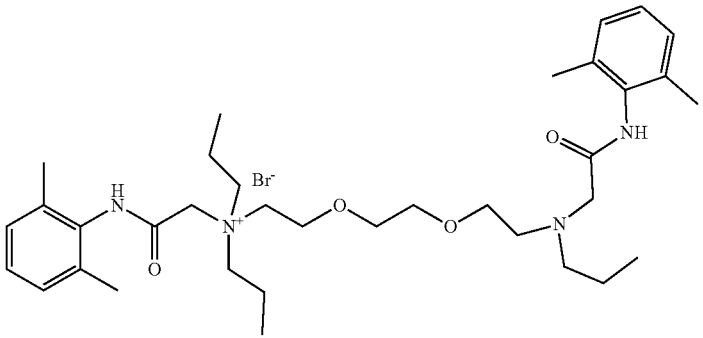<br>51 | ESI[M⁺]: 597.4 |
| 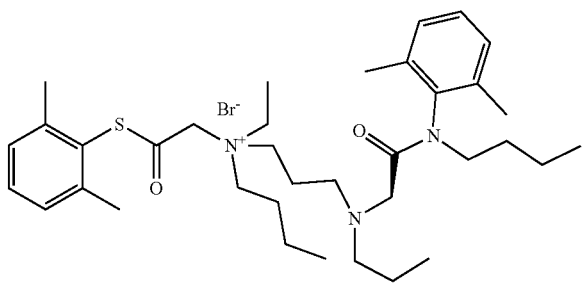<br>52 | ESI[M⁺]: 596.4 |
| 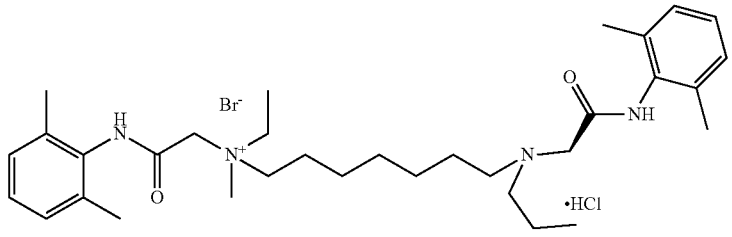<br>53 | ESI[M⁺]: 537.4 |
| 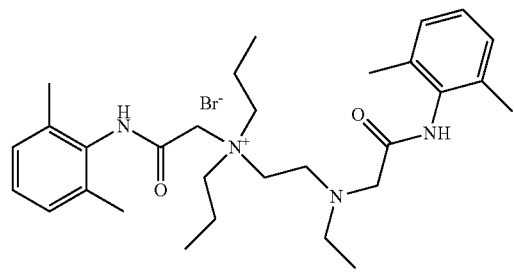<br>54 | ESI[M⁺]: 495.4 |

| Structure | Molecular formula and the molecular weight in MS |
|---|---|
| 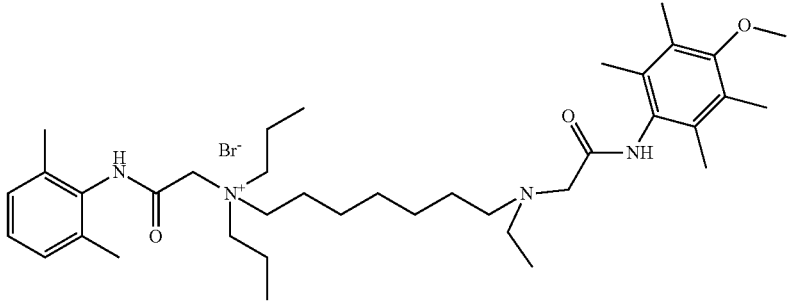<br>55 | ESI[M⁺]: 623.5 |
| 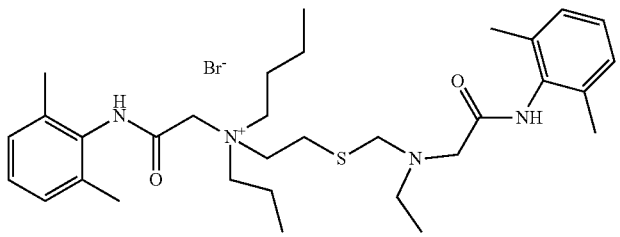<br>56 | ESI[M⁺]: 555.4 |
| 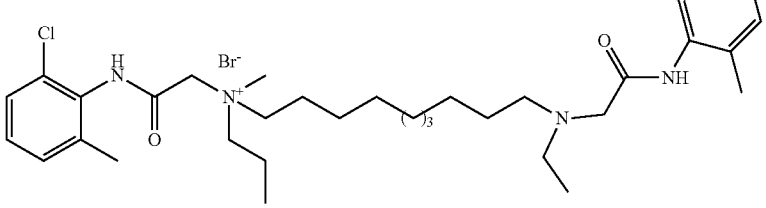<br>57 | ESI[M⁺]: 599.4 |
| 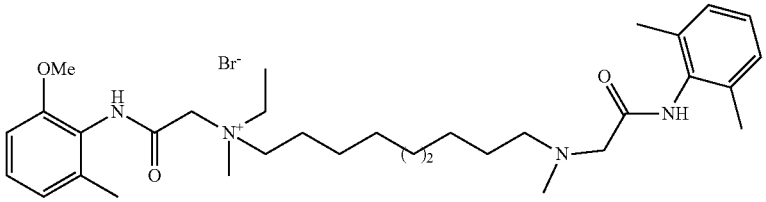<br>58 | ESI[M⁺]: 553.4 |
| 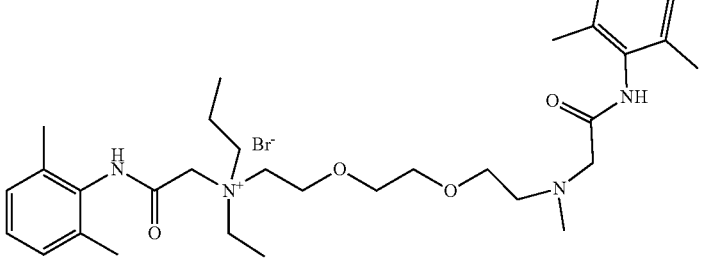<br>59 | ESI[M⁺]: 555.4 |

-continued

| Structure | Molecular formula and the molecular weight in MS |
|---|---|
| 60 | ESI[M⁺]: 525.4 |
| 61 | ESI[M⁺]: 579.5 |
| 62 | ESI[M⁺]: 495.4 |
| 63 | ESI[M⁺]: 509.4 |
| 64 | ESI[M⁺]: 551.4 |

-continued
| Structure | Molecular formula and the molecular weight in MS |
|---|---|
| 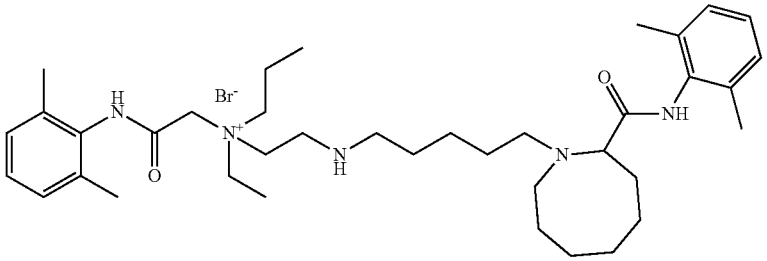<br>65 | ESI[M⁺]: 620.5 |
| 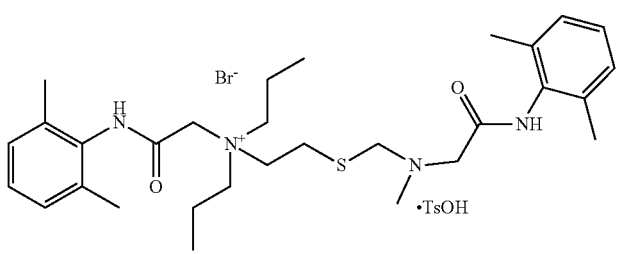<br>66 | ESI[M⁺]: 527.3 |
| 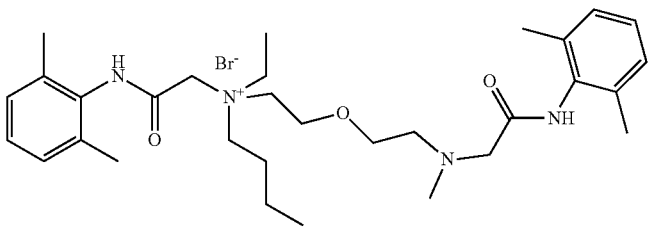<br>67 | ESI[M⁺]: 525.4 |
| 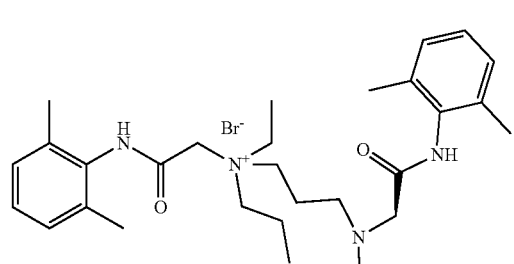<br>68 | ESI[M⁺]: 481.4 |
| 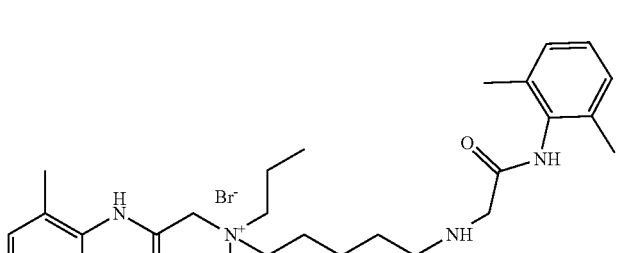<br>69 | ESI[M⁺]: 495.4 |

-continued
| Structure | Molecular formula and the molecular weight in MS |
|---|---|
| 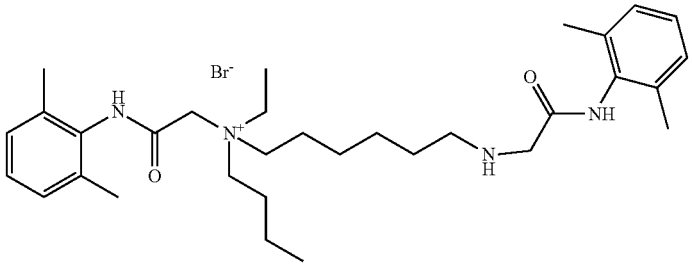<br>70 | ESI[M+]: 523.4 |
| 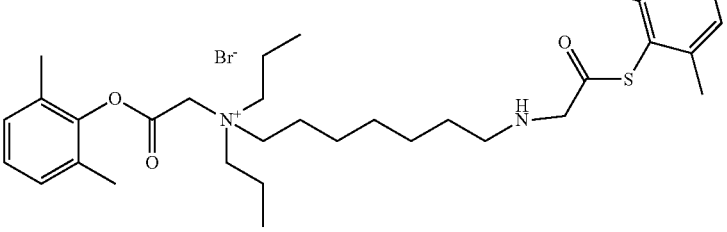<br>71 | ESI[M+]: 555.4 |
| 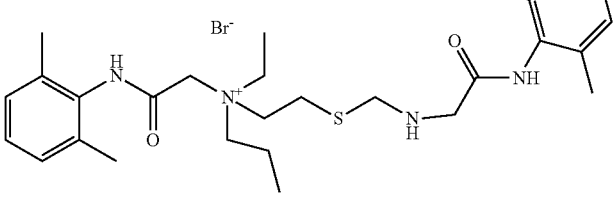<br>72 | ESI[M+]: 499.3 |
| 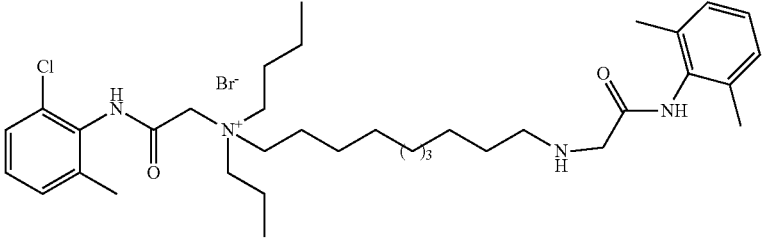<br>73 | ESI[M+]: 613.4 |
| 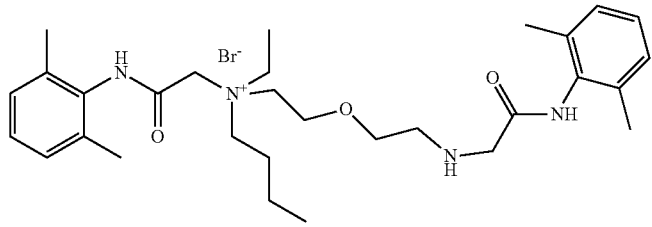<br>74 | ESI[M+]: 511.4 |

-continued

| Structure | Molecular formula and the molecular weight in MS |
|---|---|
| 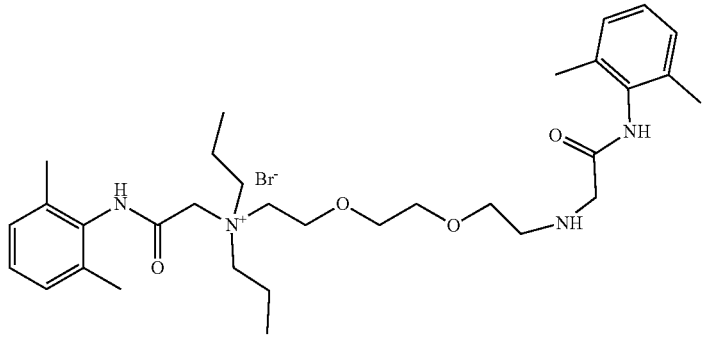 75 | ESI[M⁺]: 555.4 |
| 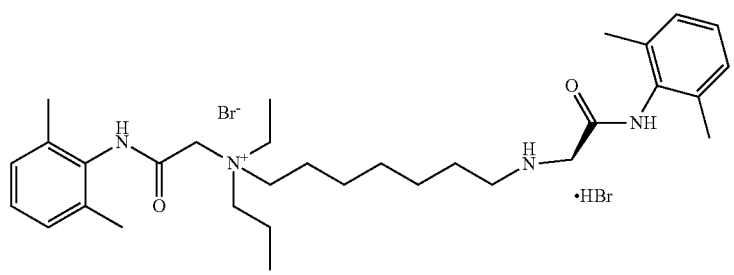 76 | ESI[M⁺]: 523.4 |
| 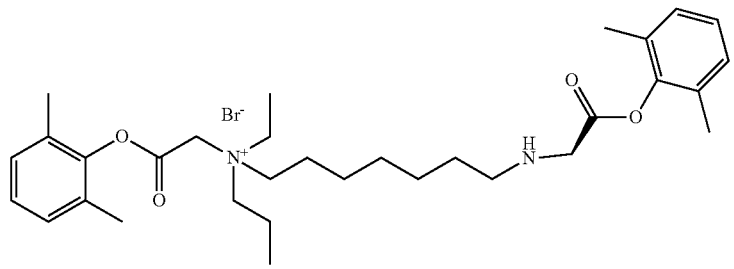 77 | ESI[M⁺]: 525.4 |

In the following, experimental examples are used to illustrate the beneficial effects of the compound of the present invention.

Experimental Example 1. Study on the Local Anesthetic Effect of the Compound of the Present Invention For selected compounds of Example 1-77, the lidocaine positive control group, and the levobupivacaine positive control group, 8 groups of test rats that were fully adapted to the experimental environment were respectively divided, 8 rats for each group.

For the dosage, the lidocaine group is 2% aqueous solution, the levobupivacaine group is 0.75% aqueous solution, and test drug groups are all distilled water solution at the concentration of 20 mmol/mL.

The injection volume for each rat or the control was 0.5 mL, which was guided by a nerve locator and injected near the rat's sciatic nerve. Using von Frey stimulator, the rats were stimulated the soles of the feet in the injected side, to observe the effect of local anesthesia. Meanwhile, Postural Extensor Thrust (PET) was used to evaluate the motor function of the rat: the rat was lifted vertically and the hindlimb in the injected side pedaled on the platform of the electronic balance. At this time, the muscle strength of the rat's hindlimb was displayed by the value on the balance caused by pedal. When the limb was completely paralyzed, the reading was the limb's own weight, about 20 g. If the measured value was more than half of the difference between the baseline and the limb weight, the motor function was regarded as recovery, and if the value was less than or equal to this difference, the motor function was regarded as loss.

TABLE 1

Local anesthetic effect of compound of the present invention on the sciatic nerve

| Test drug | Local anesthesia onset time (Median) | Time of sensory block (Median) | Time of motor block (Median) |
|---|---|---|---|
| Product in example 1 | 3 min | 24 h | 18 h |
| Product in example 2 | 2 min | 35 h | 15 h |
| Product in example 3 | 1 min | 27 h | 10 h |
| Product in example 4 | 1 min | 33 h | 10 h |
| Product in example 5 | 6 min | 28 h | 11 h |
| Product in example 6 | 3 min | 30 h | 19 h |
| Product in example 7 | 2 min | 28 h | 10 h |
| Product in example 8 | 1 min | 24 h | 18 h |
| Product in example 9 | 5 min | 24 h | 10 h |
| Product in example 10 | 2 min | 26 h | 18 h |
| Product in example 11 | 1 min | 34 h | 11 h |
| Product in example 12 | 2 min | 26 h | 19 h |
| Product in example 13 | 1 min | 25 h | 17 h |
| Product in example 14 | 3 min | 32 h | 18 h |
| Product in example 15 | 2 min | 38 h | 25 h |
| Product in example 16 | 1 min | 25 h | 19 h |
| Product in example 17 | 5 min | 24 h | 17 h |
| Product in example 18 | 1 min | 31 h | 21 h |
| Product in example 19 | 1 min | 29 h | 22 h |
| Product in example 20 | 2 min | 25 h | 20 h |
| Product in example 21 | 1 min | 24 h | 18 h |
| Product in example 22 | 3 min | 29 h | 18 h |
| Product in example 23 | 2 min | 35 h | 28 h |
| Product in example 24 | 1 min | 24 h | 16 h |
| Product in example 25 | 5 min | 32 h | 24 h |
| Product in example 26 | 3 min | 25 h | 18 h |
| Product in example 27 | 2 min | 28 h | 22 h |
| Product in example 28 | 4 min | 26 h | 18 h |
| Product in example 29 | 1 min | 33 h | 28 h |
| Product in example 30 | 4 min | 28 h | 19 h |
| Products in example 31-42 | <5 min | 25-30 h | 14-20 h |
| Products in example 43-55 | <5 min | 24-28 h | 14-18 h |
| Products in example 56-65 | <5 min | 30-35 h | 17-20 h |
| Products in example 66-77 | <2 min | 35-41 h | 21-25 h |
| 0.75% Levobupivacaine Hydrochloride | 1 min | 2.5 h | 2.5 h |
| 2% Lidocaine hydrochloride | 1 min | 1 h | 1 h |

Experimental results show that this class of drugs can produce local anesthesia lasting more than 24 h in the sciatic nerve block model, and the block time of the sensory nerve is significantly longer than that of the motor nerve, and the difference time is greater than or equal to 5 h.

Experimental Example 2. Study on the Local Anesthetic Effect of the Compound of the Present Invention After the back of rat weighing 250-300 g was shaved and disinfected, a circle with a diameter of about 1.5 cm was drawn on the side of the exposed back, and the circle is divided into 6 equal parts. 0.5 mL solution containing compounds of Examples 1-13 according to the present invention was subcutaneously injected into the skin of the center (using saline as the solvent, the concentration of bupivacaine being 23 mmol/L, and the concentration of compound of the present invention being 6 mmol/L). Among the Von Frey fiber yarns, the one with a strength of 100 g was bound to the needle for local skin stimulation. One minute After the drug was injected, the above method was used to stimulate in 6 divisions. If no back skin contraction behavior was observed in the same aliquot after three consecutive stimulations, the drug was considered to have positive effect. If back skin contraction was observed, the local anesthetic effect was considered as loss. If four or more areas in 6 aliquots showed positive local anesthesia, the local anesthesia of the drug was considered as effective, while if less than 4 areas in 6 aliquots showed positive, the local anesthesia was considered as failure. Each compound was tested with 10 rats.

TABLE 2

Local anesthetic effect of compound of the present invention by subcutaneous infiltration

| Test drug | Local anesthesia onset time (Median) | Lasting time of local anesthesia (Median) |
|---|---|---|
| Product in example 1 | 1 min | 34 h |
| Product in example 2 | 1 min | 45 h |
| Product in example 3 | 1 min | 37 h |
| Product in example 4 | 2 min | 44 h |
| Product in example 5 | 1 min | 68 h |
| Product in example 6 | 1 min | 47 h |
| Product in example 7 | 1 min | 57 h |
| Product in example 8 | 1 min | 33 h |
| Product in example 9 | 2 min | 28 h |
| Product in example 10 | 1 min | 36 h |
| Product in example 11 | 1 min | 54 h |
| Product in example 12 | 1 min | 24 h |
| Product in example 13 | 1 min | 45 h |
| 0.75% Levobupivacaine Hydrochloride | 1 min | 7 h |
| 2% Lidocaine hydrochloride | 1 min | 4 h |

Experimental results show that this class of drugs can produce local anesthesia lasting more than 24 hours in the subcutaneous infiltration model of rat.

Experimental Example 3. Study on Neuropathological Damage of Compound of the Present Invention For selected compounds of Example 1-13, the lidocaine positive control group, and the levobupivacaine positive control group, 8 groups of test rats that were fully adapted to the experimental environment were respectively divided, 8 rats for each group.

For the dosage, the lidocaine group is 2% aqueous solution, the levobupivacaine group is 0.75% aqueous solution, and test drug groups are all distilled water solution at the concentration of 20 mmol/mL. The injection volume for each rat or the control was 0.5 mL, which was injected near the rat's sciatic nerve. On day 7 and day 14 after injection near the sciatic nerve, the experimental rats were euthanized by injecting bupivacaine into the heart under isoflurane anesthesia. About 1.5 cm sciatic nerve was collected at the injection site, stored in 10% formaldehyde solution for 48 hours, stained with HE, and cut into slices with 5 μm thickness.

For the dosage, the lidocaine group is 2% aqueous solution, the levobupivacaine group is 0.75% aqueous solution, and test drug groups are all distilled water solution at the concentration of 20 mmol/mL. The injection volume for each rat or the control was 0.5 mL, which was injected near the rat's sciatic nerve. On day 7 and day 14 after injection near the sciatic nerve, the experimental rats were euthanized by injecting bupivacaine into the heart under isoflurane anesthesia. About 1.5 cm sciatic nerve was collected at the injection site, stored in 10% formaldehyde solution for 48 hours, stained with HE, and cut into slices with 5 μm thickness.

The evaluation of neuropathological damage showed that compared with the lidocaine positive control group and the levobupivacaine positive control group, compounds of Examples 1-13 did not show significant differences in the aspects of nerve injury, vascular proliferation, demyelination, muscle inflammation, and connective tissue inflammation, and thus had good safety.

In summary, the present invention provides a new class of quaternary ammonium compounds with novel structures, as well as the preparative method and the use thereof. The compound has a fast onset of action and a long-time local anesthetic effect (more than 24 hours) after a single administration. The compound was selective for nerve block (The block time of sensory nerve is longer than that of motor nerve, and the difference time is greater than or equal to 5 hours), and has both long-acting and selective local anesthetic effect, that significantly reduced the side effects of QX314, QX314 composition, and the quaternary ammonium compound with surfactant structure characteristics, with better safety. That is, the compound of formula I according to the present invention and its pharmaceutically acceptable salts can be used to prepare safe drugs with long-acting and selective local anesthesia, which has the advantages of long-time local anesthetic action, good local anesthetic selectivity, less nerve damage, and high safety.

The invention claimed is:

1. A compound of formula I, or a pharmaceutically acceptable salt thereof, or a stereoisomer thereof, or a solvate thereof, or a metabolite thereof:

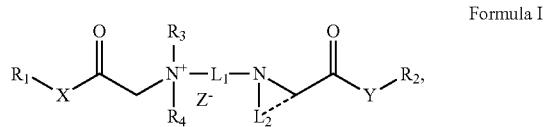

Formula I wherein,
X and Y are independently selected from O, S, and $NR_{10}$, in which $R_{10}$ is H, deuterium, or $C_{1-4}$ alkyl;
$Z^-$ is a pharmaceutically acceptable anion;
$R_1$ is an aryl substituted by a $n_1$ $R_{11}$ group;
$R_2$ is an aryl substituted by a $n_1'$ $R_{11}'$ group;
wherein, $n_1$ and $n_1'$ are independently selected from an integer of 0 to 4, and $R_{11}$ and $R_{11}'$ are independently deuterium, $C_{1-4}$ alkyls, $C_{1-4}$ alkoxys, halogen, nitro, cyano, hydroxyl, carboxyl, amino, thiol, and ester group;
with the proviso that when one of $R_3$ and $R_4$ is $C_1$ alkyl, the other is a $C_{1-4}$ alkyl;
with the proviso that when one of $R_3$ and $R_4$ is $C_2$ alkyl, the other is selected from $C_1$, $C_3$, $C_4$ alkyls;
with the proviso that when one of $R_3$ and $R_4$ is $C_3$ alkyl, the other is selected from $C_{3-4}$ alkyls;
with the proviso that when one of $R_3$ and $R_4$ is $C_4$ alkyl, the other is $C_4$ alkyl;
$L_1$ is a substituted or unsubstituted $C_{1-14}$ alkylenyl;
wherein the main chain of said alkylenyl contains 0-4 heteroatoms, and said heteroatoms are selected from O, S, and $NR_{12}$, in which said $R_{12}$ is selected from hydrogen, deuterium, $C_{1-4}$ alkyls, and $C_{1-4}$ alkoxys; said substituent is deuterium, a $C_{1-4}$ alkyl, a $C_{1-4}$ alkoxy, and a halogen;
wherein, when the dashed line in formula I is none, $L_2$ is selected from hydrogen, deuterium, substituted or unsubstituted $C_{1-8}$ alkyls, and substituted or unsubstituted $C_{1-8}$ alkoxys, in which said substituent is deuterium, a $C_{1-4}$ alkyl, a $C_{1-4}$ alkoxy, or a halogen; and wherein, when the dashed line in formula I is a bond, $L_2$ is a substituted or unsubstituted $C_{1-8}$ alkylenyl, in which the substituent is deuterium, a $C_{1-4}$ alkyl, a $C_{1-4}$ alkoxy, or a halogen.

2. The compound according to claim 1, wherein said pharmaceutically acceptable anion $Z^-$ is a halogen anion, a sulfate, an acetate, a tartrate, a p-toluenesulfonate, a methanesulfonate, or a citrate.

3. The compound according to claim 1, wherein said pharmaceutically acceptable anion $Z^-$ is a halogen anion.

4. The compound according to claim 1, wherein said pharmaceutically acceptable anion $Z^-$ is $Br^-$.

5. The pharmaceutically acceptable salt of claim 1, comprising compound of formula I and a pharmaceutically acceptable inorganic acid or organic acid.

6. The pharmaceutically acceptable salt of claim 5, wherein said inorganic acid or organic acid is selected from hydrochloric acid, hydrobromic acid, acetic acid, sulfuric acid, methanesulfonic acid, p-toluenesulfonic acid, carbonic acid, tartaric acid, lauric acid, maleic acid, citric acid, and benzoic acid.

7. The compound according to claim 1, wherein X and Y are independently selected from O, S, and $NR_{10}$, in which $R_{10}$ is H, deuterium, or a $C_{1-2}$ alkyl.

8. The compound according to claim 1, wherein, in $n_1$ $R_{11}$ and $n_1'$ $R_{11}'$, $n_1$ and $n_1'$ are independently selected from an integer of 0 to 4, and $r_{11}$ and $R_{11}'$ are independently selected from deuterium, $C_{1-4}$ alkyls, $C_{1-4}$ alkoxys, halogens, nitro, cyano, hydroxyl, carboxyl, amino, thiol, and ester group, with the proviso that when $R_3$ is a $C_1$ alkyl, $R_4$ is a $C_{1-2}$ alkyl.

9. The compound according to claim 8, wherein, $n_1$ and $n_1'$ are independently selected from an integer of 0 to 4, and $R_{11}$ and $R_{11}'$ are independently selected from deuterium, $C_{1-3}$ alkyls, methoxy, halogens, nitro, cyano, hydroxyl, carboxyl, amino, thiol, and ester group.

10. The compound according to claim 1, wherein:
$L_1$ is selected from substituted $C_{2-14}$ alkylenyls and unsubstituted $C_{2-14}$ alkylenyls;
wherein the main chain of said alkylenyl contains 0-3 heteroatoms, and said heteroatoms are selected from O, S, and $NR_{12}$, in which said $R_{12}$ is selected from hydrogen, deuterium, and $C_{1-2}$ alkyl; said substituent is selected from deuterium, $C_{1-2}$ alkyls, and $C_{1-2}$ alkoxys;
wherein,
when the dashed line in formula I is none, $L_2$ is selected from hydrogen, deuterium, unsubstituted $C_{1-8}$ alkyls, and substituted $C_{1-8}$ alkyls in which the substituent is deuterium or a $C_{1-2}$ alkyl; and
when the dashed line in formula I is a bond, $L_2$ is selected from unsubstituted $C_{2-6}$ alkylenyl and substituted $C_{2-6}$ alkylenyl in which the substituent is deuterium, a $C_{1-2}$ alkyl, or a $C_{1-2}$ alkoxy.

11. The compound according to claim 10, wherein:
$L_1$ is selected from substituted $C_{2-14}$ alkylenyls in which the substituent is selected from deuterium, $C_{1-2}$ alkyls and unsubstituted $C_{2-14}$ alkylenyls,
wherein the main chain of said alkylenyl contains 0-2 heteroatoms, and said heteroatoms are selected from O, S, and $NR_{12}$, in which said $R_{12}$ is hydrogen or deuterium,
when the dashed line in formula I is none, $L_2$ is hydrogen, deuterium, or a $C_{1-8}$ alkyl; and
when the dashed line in formula I is a bond, $L_2$ is a substituted or unsubstituted $C_{2-6}$ alkylenyl, in which the substituent is deuterium, methyl, or methoxyl.

12. The compound according to claim 1, wherein the compound is of formula II:

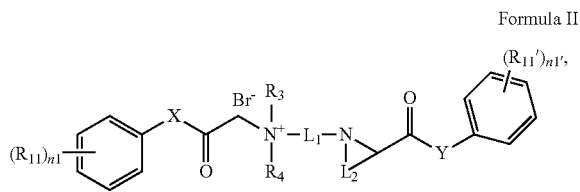

Formula II wherein:
X and Y are each independently selected from O and $NR_{10}$, in which $R_{10}$ is H, deuterium, or a $C_4$ alkyl, $R_{11}$ and $R_{11}'$ are independently selected from deuterium, $C_{1-3}$ alkyls, methoxyl, halogens, nitro, cyano, hydroxyl, carboxyl, amino, thiol, and ester group, $n_1$ and $n_1'$ are independently 2 or 3, $L_1$ is a $C_{3-14}$ alkylenyl, wherein the main chain of said alkylenyl contains 0-2 heteroatoms, and said heteroatoms are selected from O, S, and $NR_{12}$, in which said $R_{12}$ is hydrogen or deuterium, and $L_2$ is a substituted or unsubstituted $C_{2-6}$ alkylenyl, in which said substituent is methyl or methoxyl.

13. The compound according to claim 12 selected from

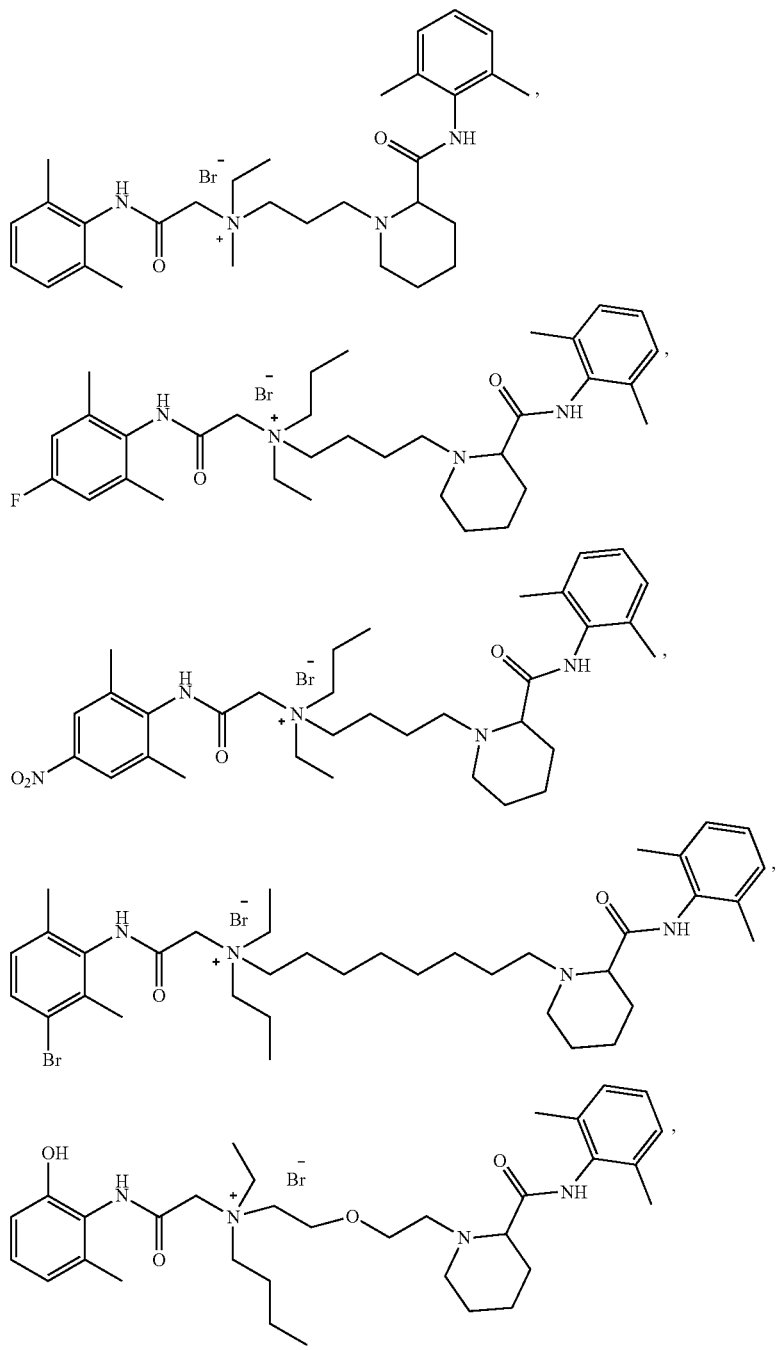

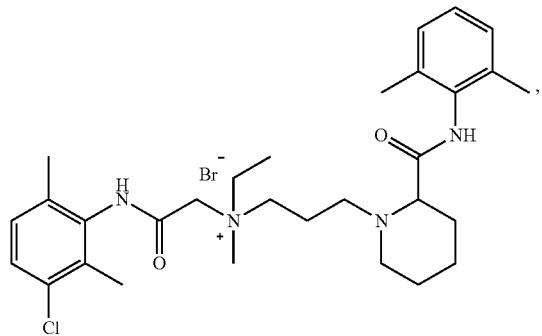
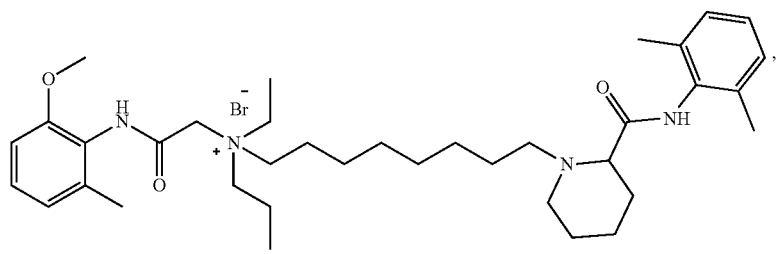
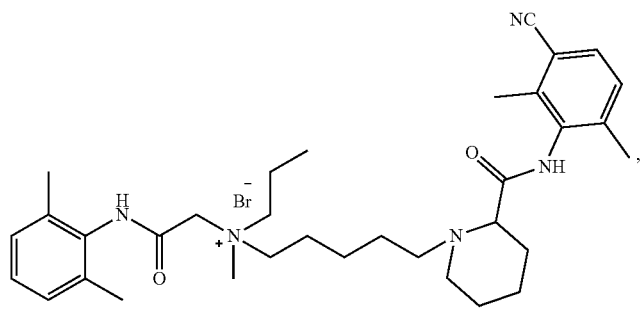
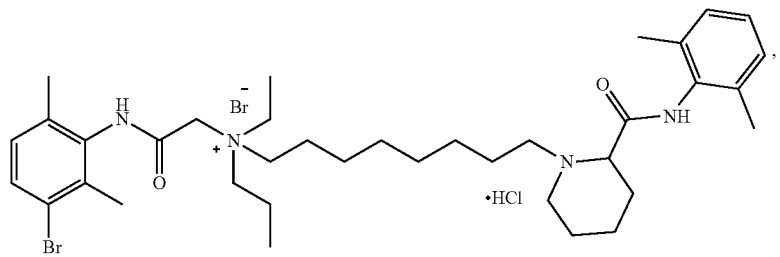
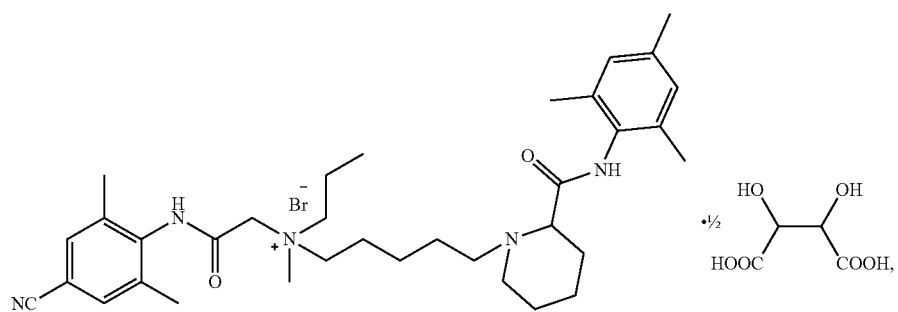

-continued
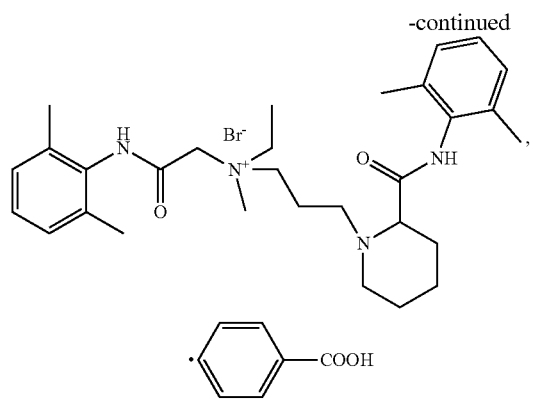
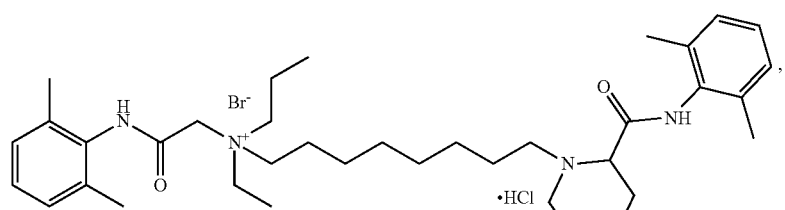
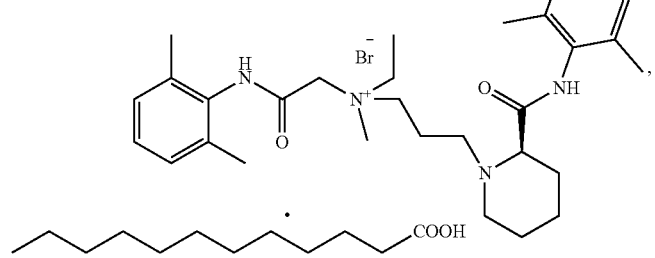
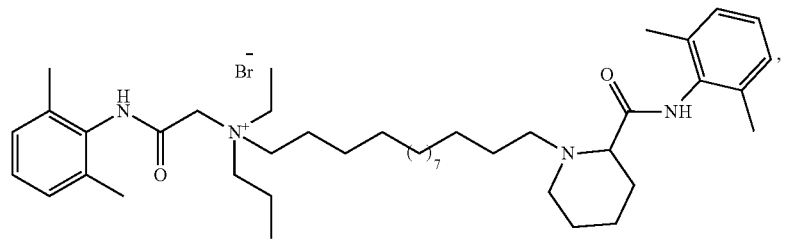
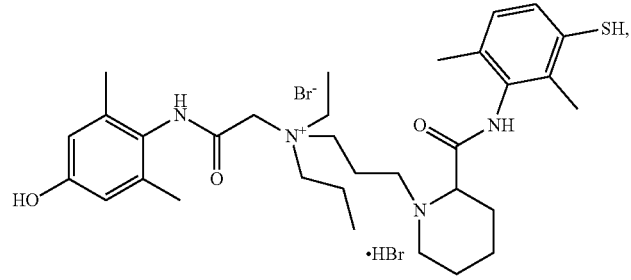
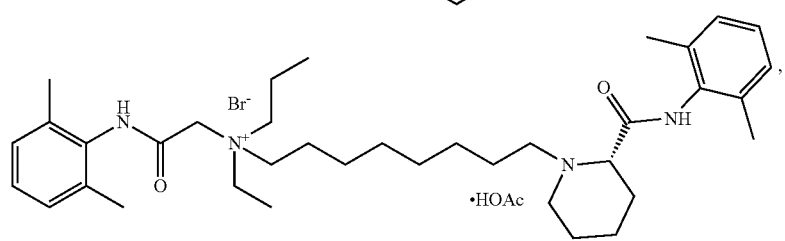

-continued
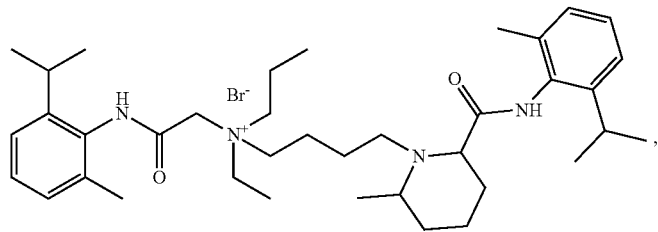
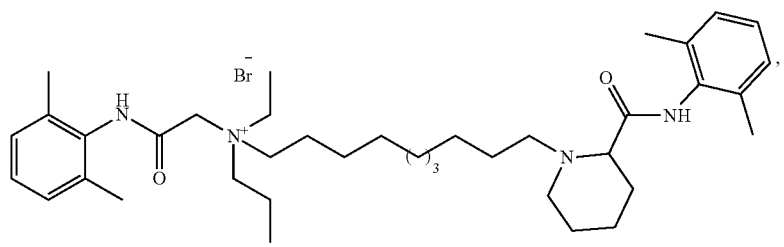
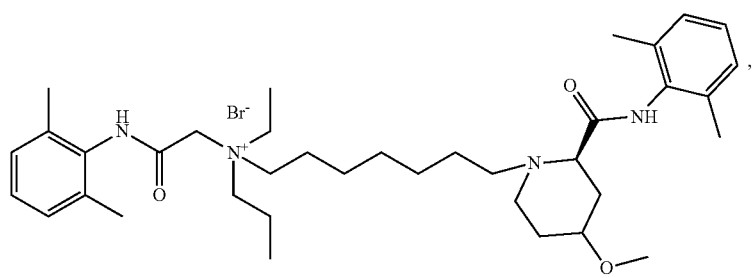
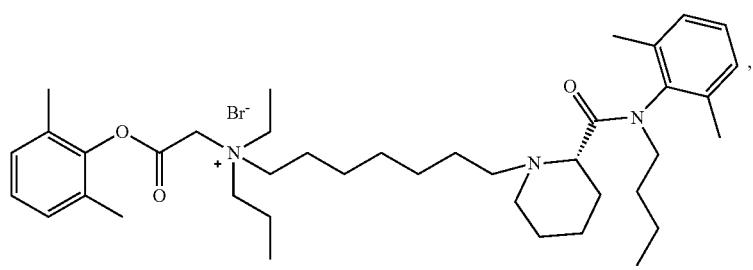
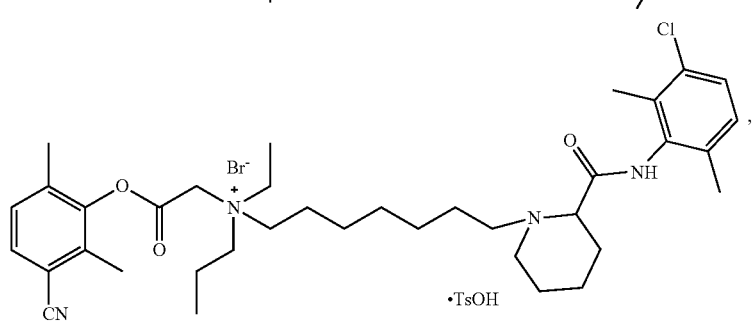
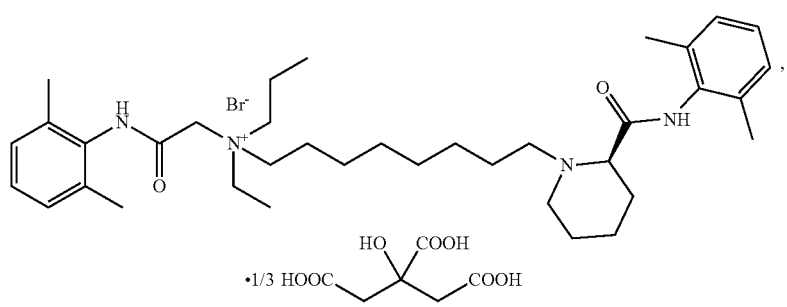

-continued
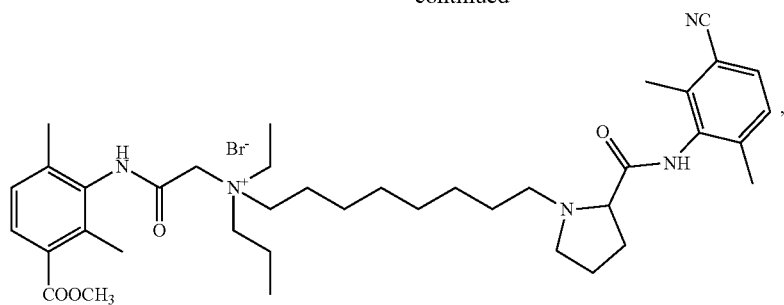
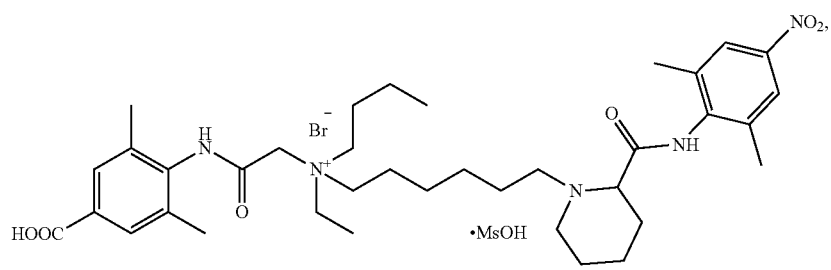
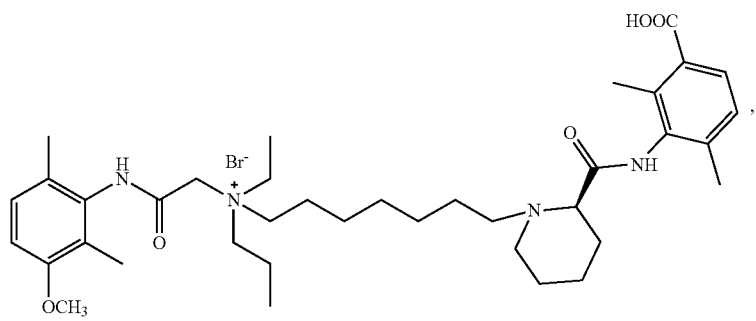
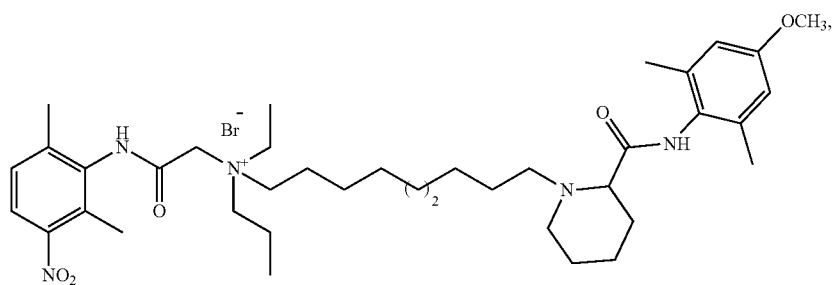
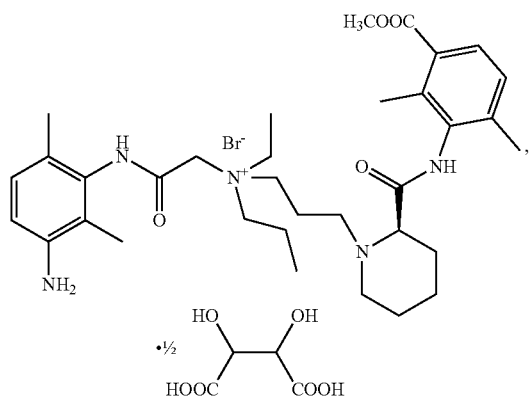

-continued
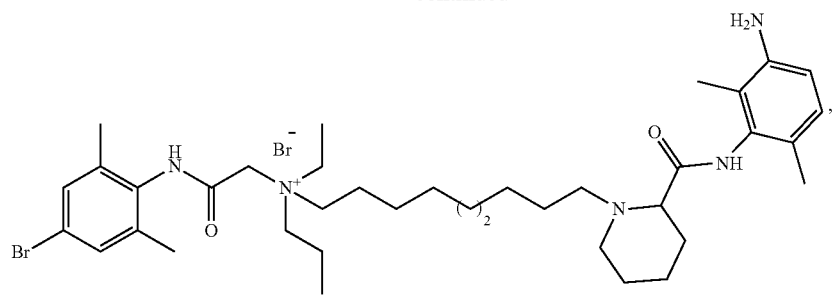
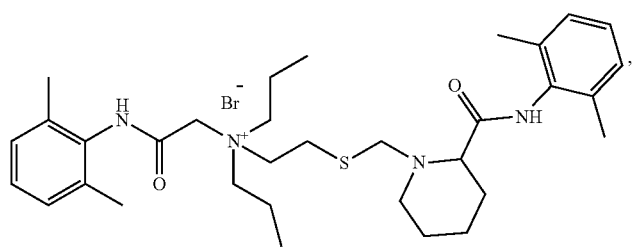
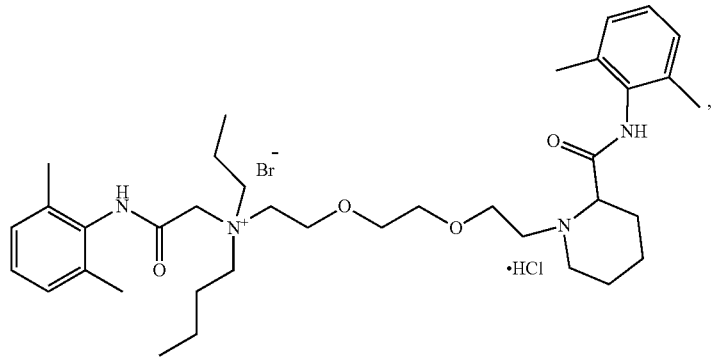
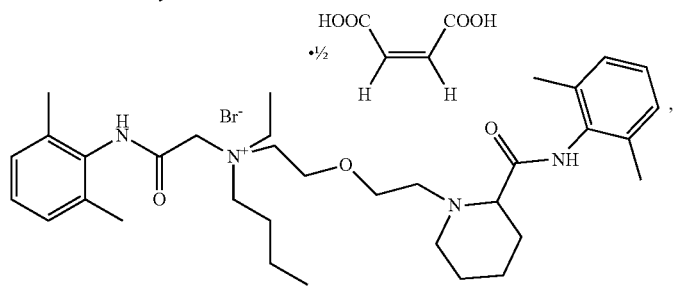
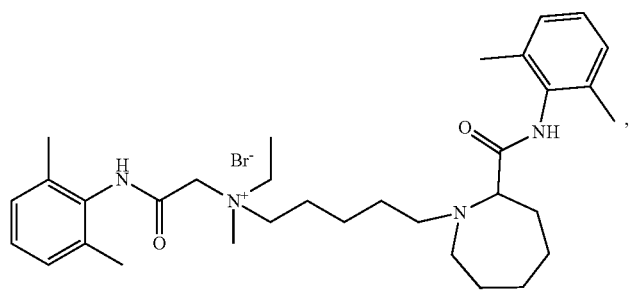
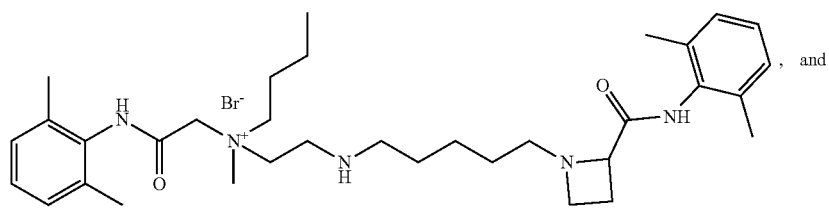

14. The compound according to claim 1, wherein the compound is of formula III:

Formula III wherein:
X and Y are each independently selected from O, S, and NR$_{10}$, in which R$_{10}$ is H, deuterium, or a C$_4$ alkyl;

R$_{11}$ and R$_{11}$' are independently selected from deuterium, C$_1$ alkyl, methoxyl, and halogens;

n$_1$ and n$_1$' are independently of selected from an integer of 2-4;

L$_1$ is a C$_{2-10}$ alkylenyl;

wherein the main chain of said alkylenyl contains 0-2 heteroatoms, and said heteroatoms are selected from O, S, and NR$_{12}$, in which said R$_{12}$ is hydrogen or deuterium; and L$_2$ is selected from H, deuterium, and C$_{1-8}$ alkylenyls.

15. The compound according to claim 1 selected from

-continued
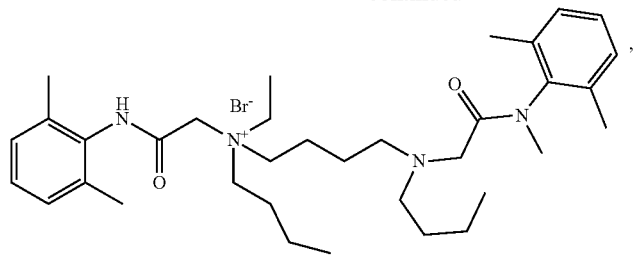
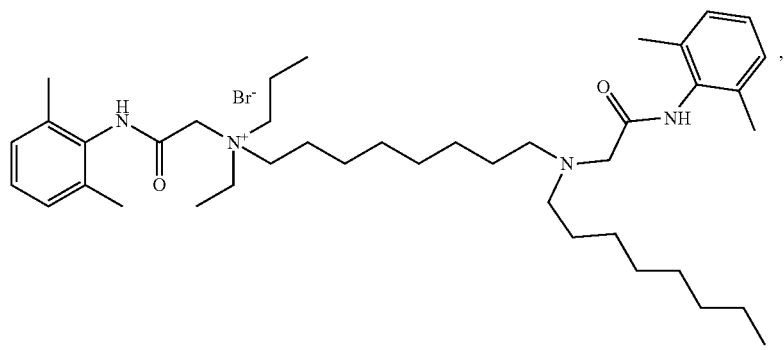
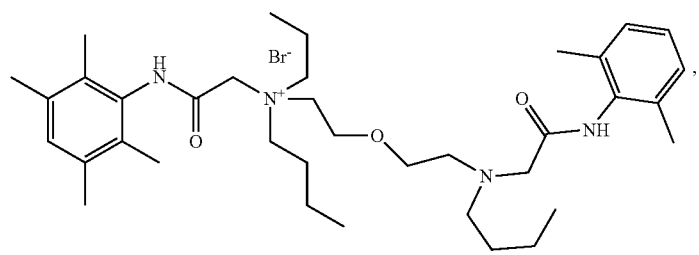
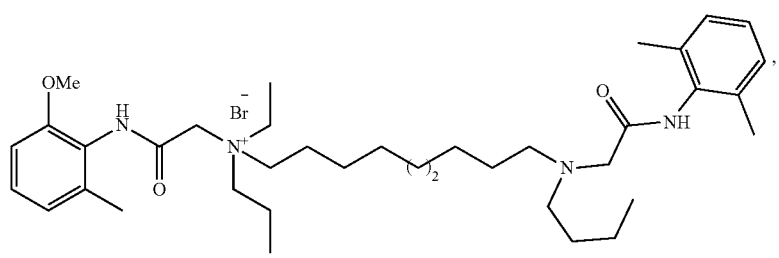
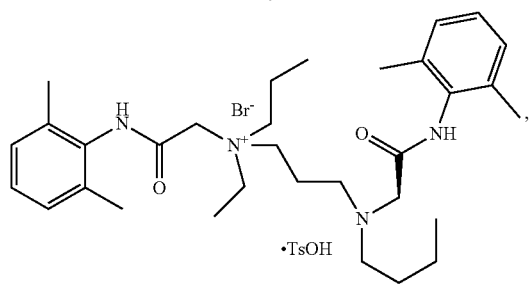
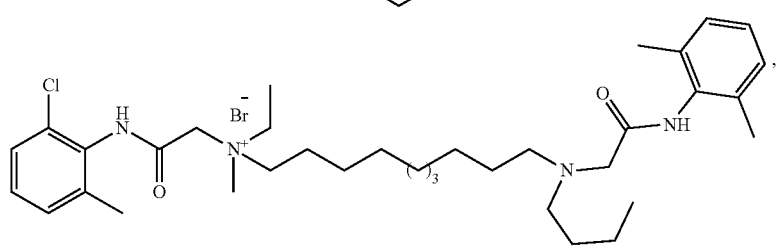

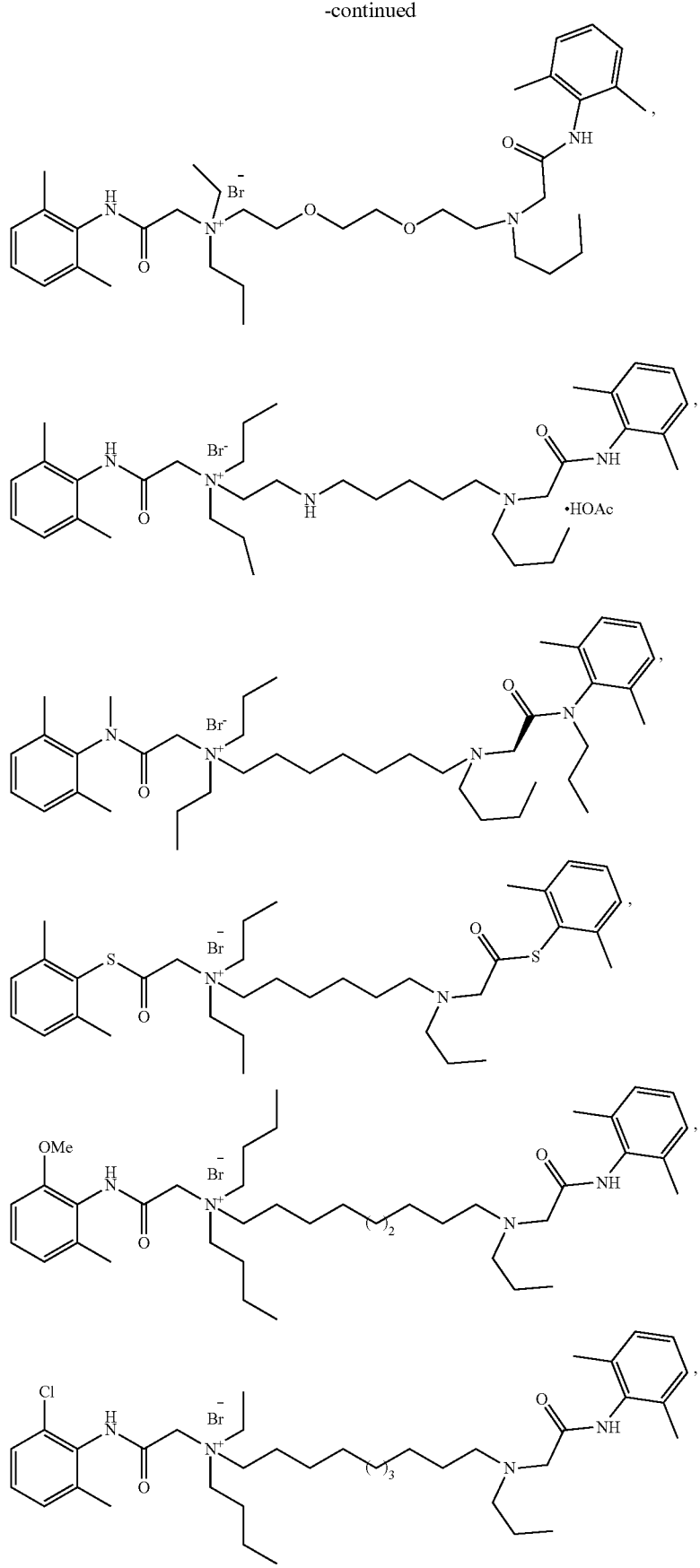

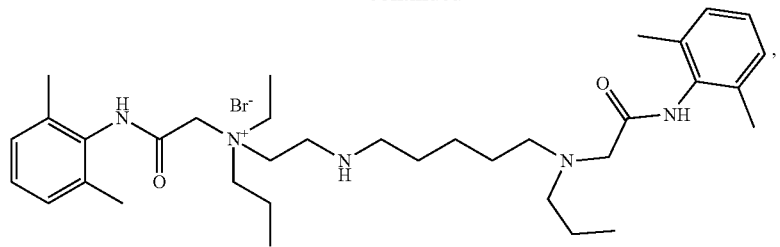
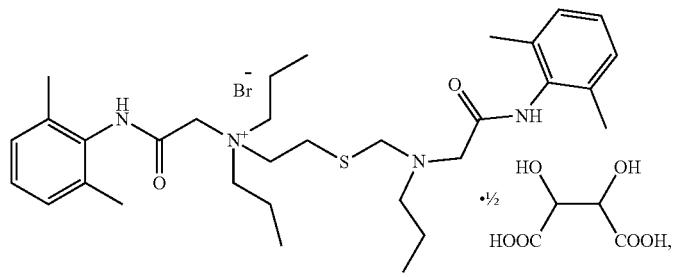
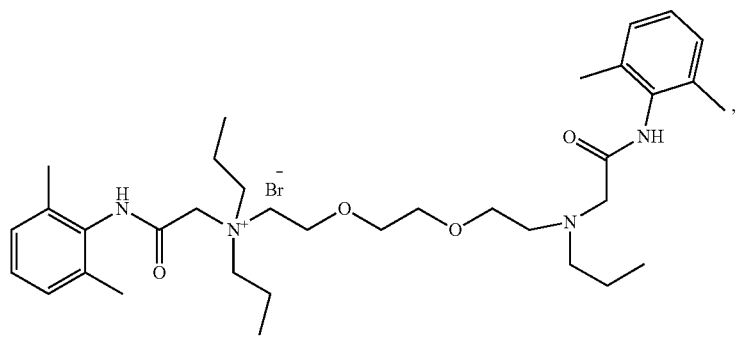
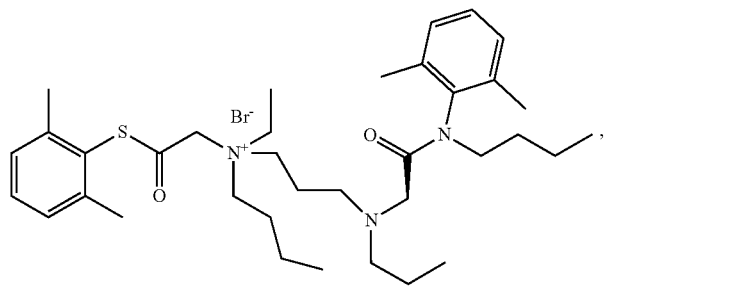
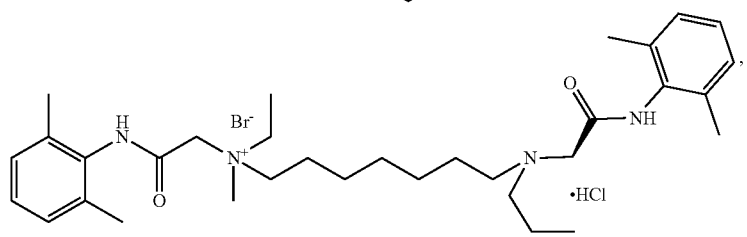
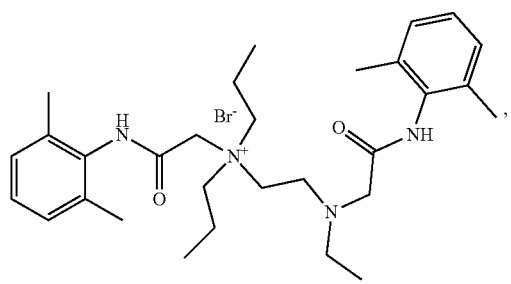

-continued
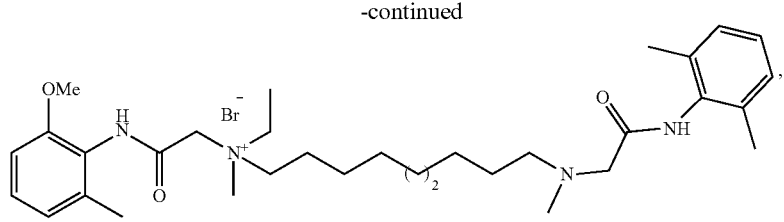
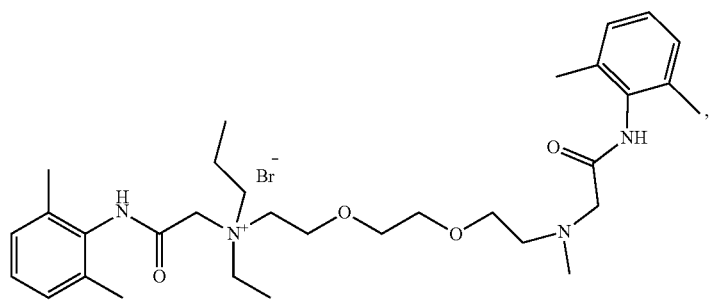
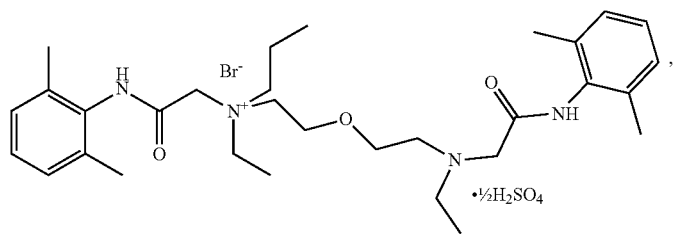
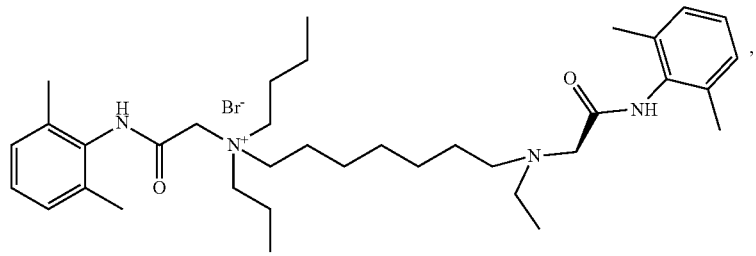
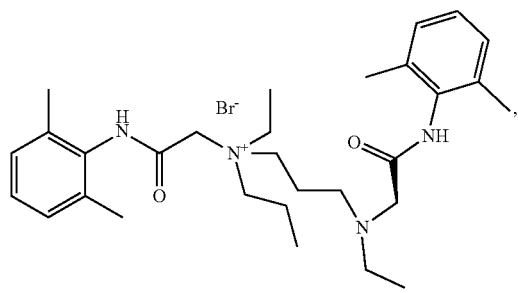
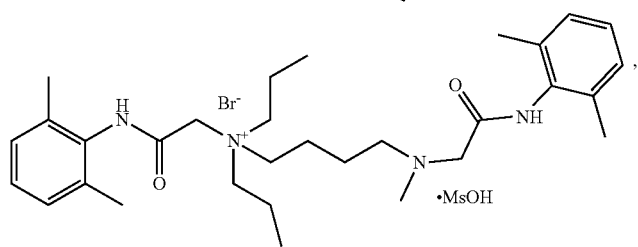

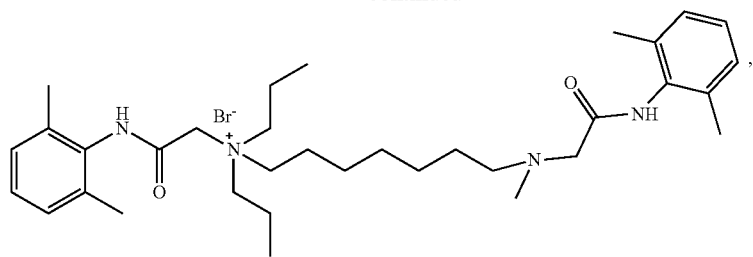
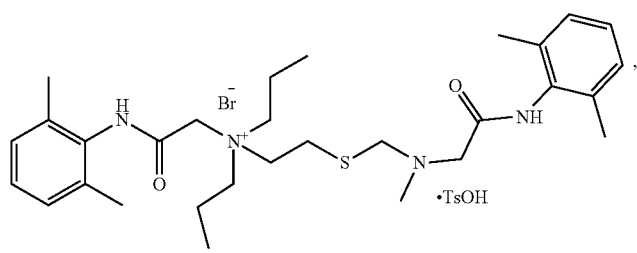
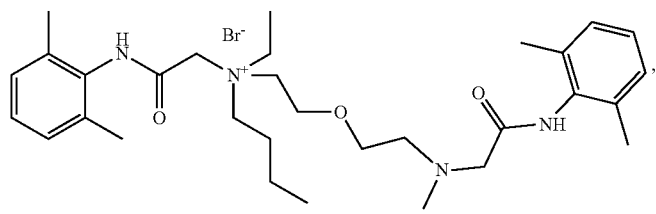
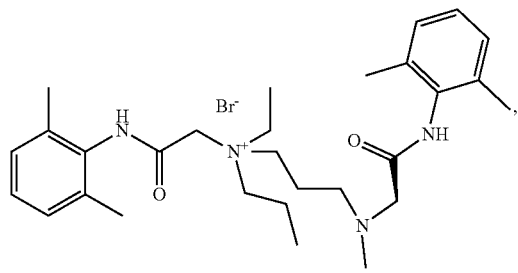
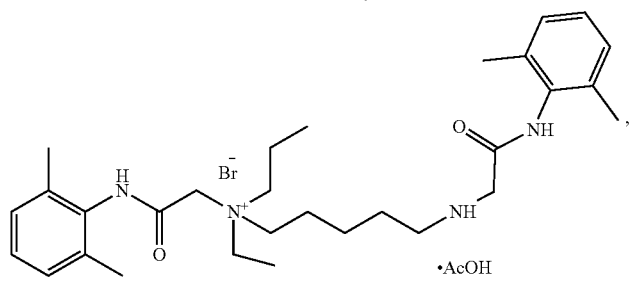
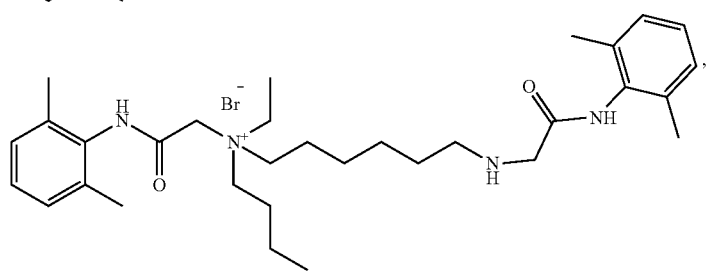

-continued
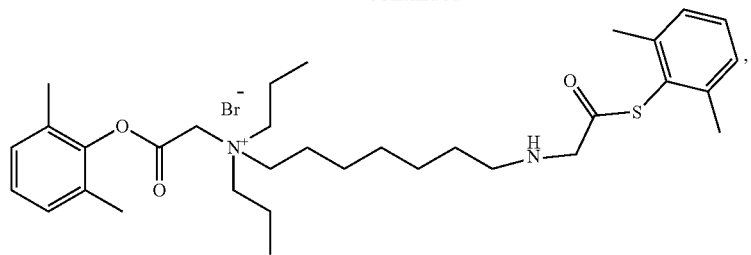
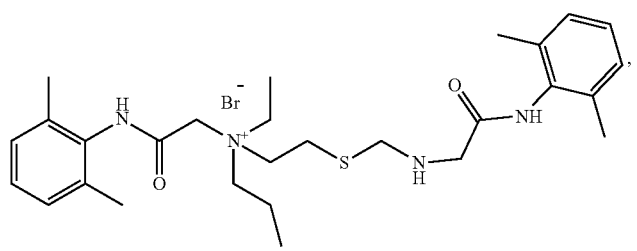
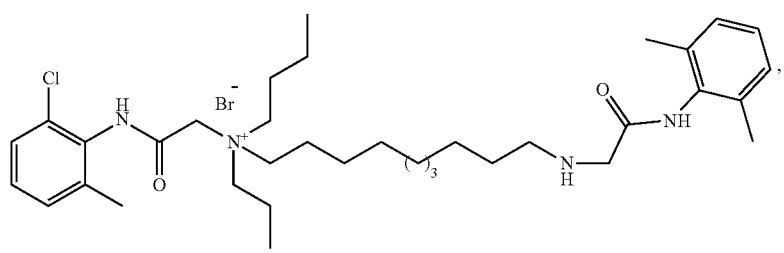
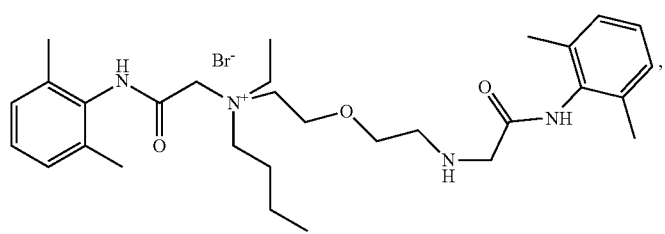
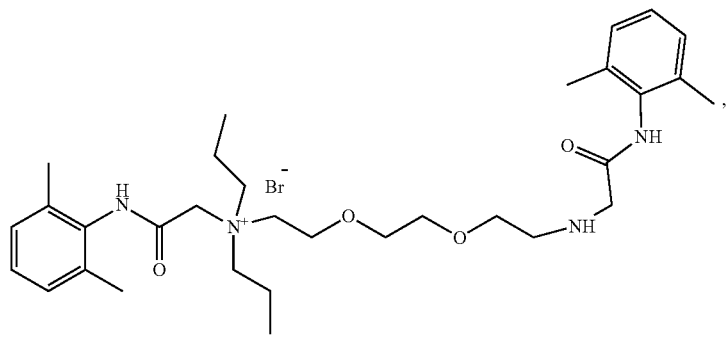
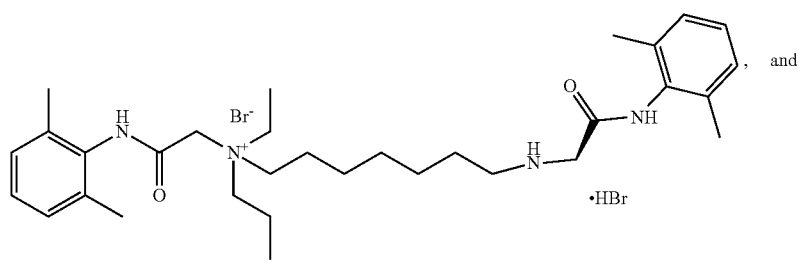

-continued

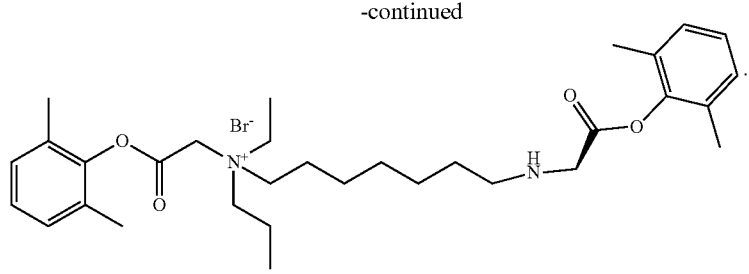

16. A method for preparing compound according to claim 1, or pharmaceutically acceptable salts thereof, or stereoisomers thereof, or solvates thereof, or metabolites thereof, comprising the step of reacting the quaternary ammonium compound of formula IV with the amine compound of formula V in the presence of a base to obtain the target compound of formula I:

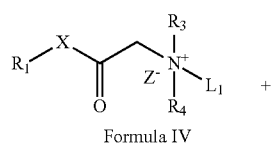

Formula IV

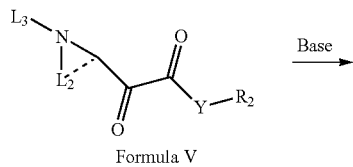

Formula V

-continued

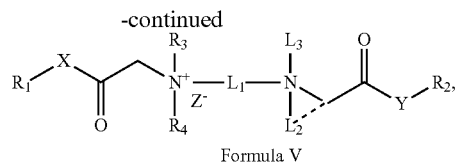

Formula V wherein $L_3$ in formula V is hydrogen.

17. The preparative method according to claim 16, wherein said base is an inorganic base or an organic base, and wherein said inorganic base is potassium carbonate or cesium carbonate; and said organic base is triethylamine or 1,8-diazabicycloundec-7-ene.

18. The preparative method according to claim 16, wherein said reaction is carried out in a polar protic solvent.

19. The preparative method according to claim 18, wherein said solvent is methanol or ethanol.

20. A drug comprising the compound of formula I, or the pharmaceutically acceptable salt thereof, or the stereoisomer thereof, or the solvate thereof, or the metabolite thereof according to claim 1, and one or more pharmaceutically acceptable adjuvants.

* * * * *